United States Patent [19]
Wertz

[11] Patent Number: 5,612,894
[45] Date of Patent: Mar. 18, 1997

[54] SYSTEM AND METHOD FOR MOLECULAR MODELING UTILIZING A SENSITIVITY FACTOR

[76] Inventor: David H. Wertz, 169 Snowden La., Princeton, N.J. 08540

[21] Appl. No.: 390,600

[22] Filed: Feb. 8, 1995

[51] Int. Cl.⁶ ................................................. G06F 17/50
[52] U.S. Cl. .......................................... 364/496; 364/578
[58] Field of Search ..................................... 364/496–499, 364/578, 527, 524

[56] References Cited

U.S. PATENT DOCUMENTS

| | | |
|---|---|---|
| 4,855,931 | 8/1989 | Saunders . |
| 4,908,781 | 3/1990 | Levinthal et al. ................. 364/524 |
| 5,008,831 | 4/1991 | Feldman . |
| 5,025,388 | 6/1991 | Cramer . |
| 5,159,682 | 10/1992 | Toyonaga et al. ................. 395/500 |
| 5,200,910 | 4/1993 | Subbiah . |
| 5,307,287 | 4/1994 | Cramer, III et al. ................. 364/496 |
| 5,438,526 | 8/1995 | Itoh et al. ................. 364/578 |
| 5,448,498 | 9/1995 | Namiki et al. ................. 364/496 |
| 5,463,564 | 10/1995 | Agrafiotis et al. ................. 364/496 |

FOREIGN PATENT DOCUMENTS

WO92/01933  2/1992  European Pat. Off. .

*Primary Examiner*—Emanuel T. Voeltz
*Assistant Examiner*—Kyle J. Choi
*Attorney, Agent, or Firm*—Kenyon & Kenyon

[57] ABSTRACT

A computerized molecular modeling system is provided which graphically displays at least an initial and most likely structure of a molecule utilizing energy minimization and/or molecule dynamics techniques. The system utilizes a sensitivity factor to determine how often the less sensitive interactions, especially non-bonded interaction in a molecule should be recalculated during an energy minimization or molecular dynamics procedure. The sensitivity factor is based on each interaction's sensitivity to changes in the positions of the atoms that comprise it.

8 Claims, 11 Drawing Sheets

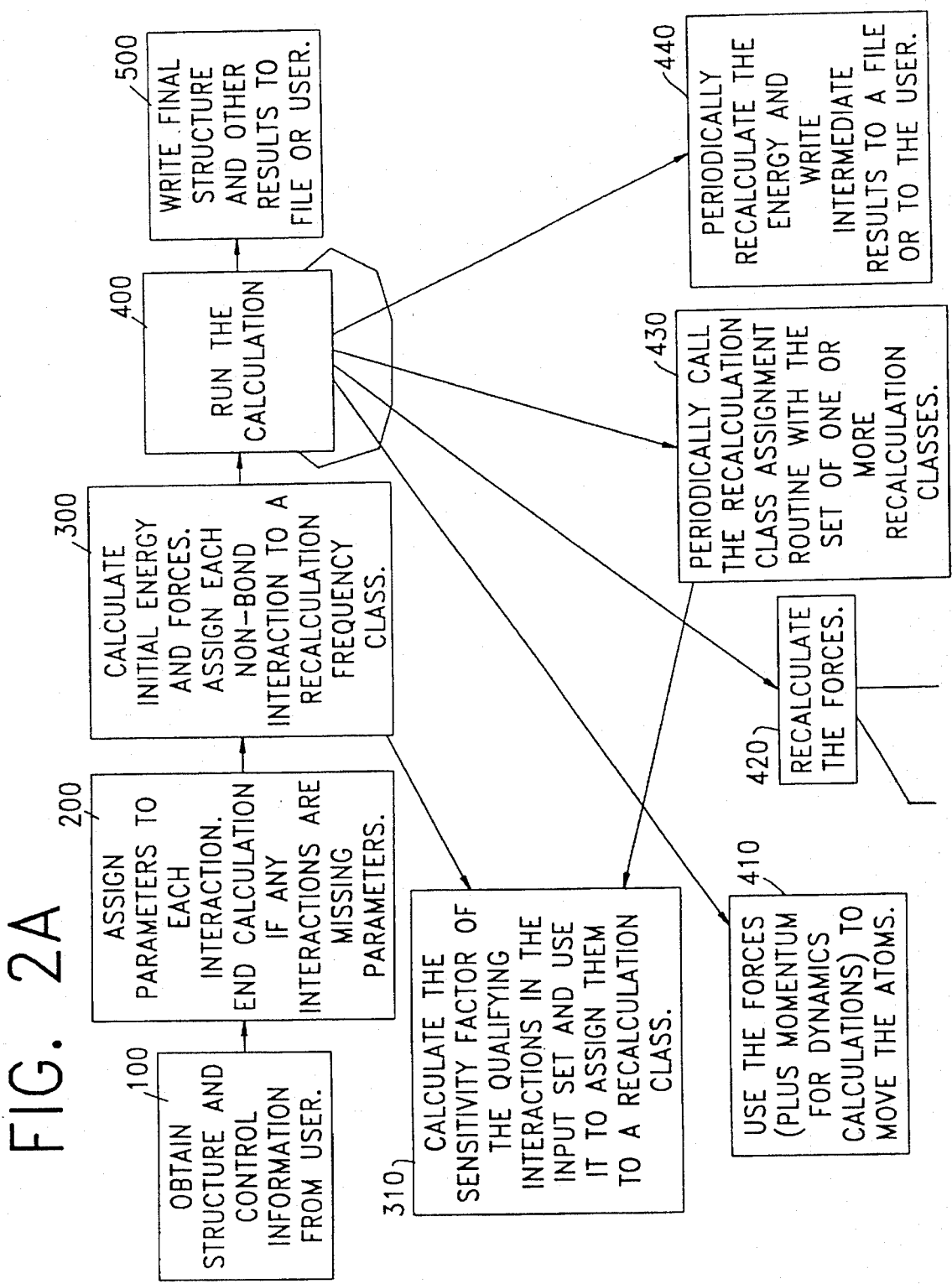

$$E = \sum_{bonds} \frac{1}{2} k_b (l_b - l_b^0)^2 + \sum_{angles} \frac{1}{2} k_\theta (\theta - \theta^0)^2 +$$

$$\sum_{torsion} k_3(1+\cos(3\theta - \beta_3)) + k_2(1+\cos(2\theta - \beta_2)) + k_1(1+\cos(\theta - \beta_1)) +$$

$$\sum_{non-bonds} \frac{q_I q_J}{R_{I,J}} + \frac{A_{I,J} R_{I,J}^{0\,6}}{R_{I,J}^6} + \frac{B_{I,J} R_{I,J}^{0\,12}}{R_{I,J}^{12}} + \sum_{H-bonds} \frac{C_{I,J} R_{I,J}^{0\,10}}{R_{I,J}^{10}} + \frac{D_{I,J} R_{I,J}^{0\,12}}{R_{I,J}^{12}}$$

FIG. 3

ETHANE1

| | X | Y | Z |
|---|---|---|---|
| 1 C1 | −4.53003 | 1.35455 | −2.44732 |
| 2 H2 | −4.73433 | 2.38928 | −2.67971 |
| 3 H3 | −5.44266 | 0.85687 | −2.15437 |
| 4 C4 | −3.51317 | 1.27218 | −1.31650 |
| 5 H5 | −4.12641 | 0.86782 | −3.32288 |
| 6 H6 | −3.90529 | 1.75593 | −0.43411 |
| 7 H7 | −2.59335 | 1.75164 | −1.61725 |
| 8 H8 | −3.31508 | 0.23427 | −1.09308 |

| ETHANE2 | X | Y | Z |
|---|---|---|---|
| 1 C1 | −4.10303 | 1.40863 | −3.32656 |
| 2 H2 | −4.17857 | 2.46175 | −3.55379 |
| 3 H3 | −4.98836 | 0.89438 | −3.67025 |
| 4 C4 | −3.94698 | 1.21633 | −1.82382 |
| 5 H5 | −3.23843 | 0.99917 | −3.82780 |
| 6 H6 | −4.75736 | 0.61125 | −1.44495 |
| 7 H7 | −3.94775 | 2.17731 | −1.33095 |
| 8 H8 | −3.00979 | 0.71742 | −1.62592 |

| ETHANE2 | | X | Y | Z |
|---|---|---|---|---|
| 1 | C1 | −4.58583 | 1.39705 | −3.08818 |
| 2 | H2 | −4.71816 | 2.44537 | −3.31160 |
| 3 | H3 | −5.51282 | 0.97934 | −2.72403 |
| 4 | C4 | −3.49721 | 1.22845 | −2.03651 |
| 5 | H5 | −4.29245 | 0.87727 | −3.98827 |
| 6 | H6 | −3.90069 | 0.73129 | −1.16678 |
| 7 | H7 | −3.10787 | 2.19598 | −1.75598 |
| 8 | H8 | −2.69734 | 0.63024 | −2.44732 |

| 1☆ | 2 | 3 | 4☆ | 5 | 6 | 7 | 8 | 9 | 10☆ |

| 11 | 12 | 13 | 14 | 15 | 16☆ | 17 | 18 | 19 | 20☆ |

End of atom 1's full bit set

| 21 | 22 | 23 | 24 | 25☆ | 26 | 27 | 28 | 29 | | . . . .

End of atom 2's full bit set

☆ Indicates a word with non-zero bits

SYSTEM AND METHOD FOR MOLECULAR MODELING UTILIZING A SENSITIVITY FACTOR

FIELD OF THE INVENTION

The present invention relates to computerized molecular modeling systems used to determine the structure, shape, and properties of molecules and aggregates of molecules. The present invention further relates to a molecular modeling system that decreases the amount of computer time and computer memory required to minimize the energies of molecules and to perform molecular mechanics calculations.

BACKGROUND OF THE INVENTION

When conducting research in the field of chemistry, or even teaching chemistry to a student, it is often useful to visualize the structure, or shape, of a molecule.

In the past, when chemists wanted to visualize the shape of a molecule, the chemist built a physical model of the molecule using, for example, molecular structural models comprised of interconnectable plastic balls (representing atoms) and sticks (representing bonds). Not only was the construction of such models a tedious and time consuming task, but, moreover, the calculations required to determine the proper coordinates of the balls were also highly time consuming.

Recently, the use of computer graphics terminals has greatly simplified the task of determining the structure, shape, and properties of molecules. Various graphics systems are currently available for use in generating molecular models. Such systems include the Chem-X, Sybyl, Quanta, and CSC Chem3D systems. While the features of these systems vary to some extent, each provides a graphical representation illustrating the shape of molecules. With, for example, the Chem-X system, a user can create a graphical representation of a molecule in several ways:

1. The User can draw his/her own molecule using, for example, a keyboard and mouse;

2. The User can input experimental data which represents the structure of an actual molecule;

3. The User can retrieve a previously stored molecular structure.

Once the initial structure of a molecule is entered into the system in one of these three ways, then an energy minimization (or molecular dynamics) technique can be used to find the most likely structure of the molecule.

A trained chemist can learn a great deal from looking at the structures of molecules on a computer graphics terminal. For example, biologically active molecules often act by binding to a region of a protein known as the active site. By looking at the minimum energy structures of a set of molecules that bind to an active site, a chemist might be able to determine what features of the molecules were responsible for both good and poor binding energies. He or she could then use this information to propose new molecules that combined the good features of two or more molecules or even propose features that were not present in any of the original molecules.

A trained chemist can also learn a great deal from using a graphics terminal to look at how the atoms in a molecule move during a molecular dynamics calculation. When this is done, the chemist is able to see what is in essence a moving picture of the molecule in action. Since molecules do move and such motions can affect their properties, viewing a molecular dynamics simulation as it evolves can be more informative than looking at still shots of the molecule.

In determining the structure, shape, and thermodynamic properties of molecules and aggregates of molecules, chemists generally calculate the energy of the molecules. The structure and thermodynamic properties are important because they affect many of the other properties of a molecule. For example, the activity of a drug molecule depends on its ability to bind to an active site. Binding occurs only if the shape of the drug molecule allows it to fit into the active site and the binding energy is favorable.

Although the properties obtained from energy calculations can usually be determined experimentally, energy calculations are useful adjuncts to experiments because experiments are time consuming and expensive. An additional advantage of energy calculations is that they can help the chemist in understanding why changes in the molecular structure cause the properties of the molecules to change, while experiments usually reveal only what the change is. Knowing why the properties of existing molecules vary can be very useful in developing new molecules with more desirable properties.

It is generally accepted that the most accurate and reliable energy calculation method is complete quantum mechanics done without using approximations. Doing quantum mechanics without approximations means doing ab initio calculations with an extremely large number basis functions and doing configuration interaction calculations that involve all possible combinations of excited states. Unfortunately, such complete calculations are so computationally intensive that they are seldom done.

Currently ab initio calculations are typically done using a basis set with a moderate number of basis functions and using only a few excited states. Such medium level calculations are felt to give the best trade-off between reliability and cost. Even these medium level calculations, however, take a significant amount of computer time. For example, an ab initio calculation of benzene, which contains 6 carbon atoms and 6 hydrogen atoms, with the RHF/6-31+G basis set and configuration interactions involving only 8 singly excited states requires 2.5 hours on a computer with an Intel™ 80486DX2 CPU running at 66 MHz.

The calculation discussed above involved only a single calculation of the energy of a molecule with a fixed geometry. If the geometry had been optimized to find the lowest energy structure the calculation would have been from 10 to 100 times longer. (Note that the terms geometry optimization and energy minimization are interchangeable in the context of this discussion.) Quantum mechanics molecular dynamics calculations take at least 10 times longer than geometry optimizations and are so time consuming that they are seldom performed. In addition, since the mount of computer time required to do a calculation increases as the 4th power of molecular size, even medium level ab initio calculations are usually confined to molecules with less than 20 nonhydrogen atoms. An illustration of the combined effect of increasing the number of atoms and optimizing the geometry is that the geometry optimization of a molecule containing 22 nonhydrogen atoms required over a week of CPU time on a Cray™ supercomputer. Cray supercomputers are over 10 times faster than Intel 80486 based computers.

For medium or large molecules, either approximate quantum mechanics methods are used, which reduce the reliability of the calculation, or less expensive methods, such as molecular mechanics, are used.

Molecular mechanics calculations are much faster and cheaper than complete quantum mechanics calculations, and, when used properly, molecular mechanics calculations can approach the accuracy of complete quantum mechanics calculations. Thus they are often the best calculation method for medium sized molecules and are usually the only practical method for large molecules or aggregates of molecules.

Both quantum mechanics and molecular mechanics methods require an initial structure of a molecule. The two most common methods of describing initial structures are Cartesian coordinates and Z-coordinates. The Cartesian coordinate method gives the location of each atom relative to a set of Cartesian coordinates and often includes a list identifying which atoms are bonded to each other. In situations where the bond lengths are known to have typical values, the bond list can be derived from the coordinates. The Z-coordinate method identifies the atoms making up each bond and its length, the atoms making up each bond angle and its value, and the atoms making up each torsional angle and its value. These two methods of describing the molecule contain the same information—each can be generated from the other. It is usually more convenient to do calculations using Cartesian coordinates. Thus Z-coordinates are usually converted into Cartesian coordinates at the start of a computation. People, however, find Z-coordinates easier to understand and calculated structures are often converted into Z-coordinates for display purposes.

Molecular mechanics calculations fall into two categories: energy minimizations and molecular dynamics.

In accordance with energy minimization techniques, the position of each atom is varied over a plurality of iterations until a minimum in the energy of the molecule, as determined by the force field, is found. This static, minimum energy structure, is then taken to represent what occurs in an experiment. This corresponds to doing an experiment in a vacuum at absolute zero. Even though very few experiments are done under these conditions, it has been empirically determined that the time averaged structure of a particular conformation of a molecule is usually similar to that conformation's minimum energy structure.

Molecular dynamics calculations integrate Newton's second law to reproduce the dynamics and movement of the atoms in both single molecules and aggregates containing many molecules. The advantage of molecular dynamics, as opposed to energy minimizations, is that it reproduces the dynamic nature of molecules. For example, if there are many conformations, a molecule will visit all of them during a properly conducted molecular dynamics calculation and the calculated properties will be a statistical average of all the conformations. The ability to obtain average values is important because experimental properties are usually obtained from a sample containing an extremely large number of molecules. Thus, experimental values are averages. The averages that can be obtained from molecular dynamics calculations are believed to be a better approximation of experimental values than the values for a single structure obtained from minimizations.

The large number of terms that must be evaluated in molecular mechanics calculations causes minimizations and molecular dynamics calculations of large molecule to take hours or even days on even the fastest computers. Thus, while molecular mechanics calculations are less expensive than quantum mechanics calculations, they can still be time consuming and expensive. As such, molecular mechanics calculations, while less computationally intensive than quantum mechanics calculations, can be too time consuming for effective use with large molecules in computerized molecular modeling systems.

Consequently, a need existed to design a computer system that reduced the computer time required for such calculations. Thus most programs that perform molecular mechanics calculations use standard techniques for increasing the efficiency of the calculations, such as calculating mathematical expressions that occur in more than one place only once and using methods like those described in J. Bentley, "Writing Efficient Programs" (192). However, such standard techniques are not sufficient to produce the speed increases needed. Thus additional techniques are needed. Since most of the computer's processing time is spent calculating non-bonded interactions, these interactions have received the most attention. The term "interaction" refers to a relationship between atoms, and, in the context of molecular modeling, interactions are generally used to refer to a force or energy that varies depending on the distance and/or orientation of two or more atoms relative to each other.

Two methods have been widely used in both minimizations and molecular dynamics calculations to reduce the time spent calculating non-bonded interactions.

One method takes advantage of the fact that forces between widely separated atoms are small. This method establishes a distance, known as the cut-off distance, and all forces between atoms separated by distances greater than the cut-off distance are assumed to be zero and not calculated. This method was found to be adequate when electrostatic interactions are negligible. However, when electrostatics are important, it was found that a large cut-off distance is required in order for the results to agree with calculations performed without a cut-off distance. Unfortunately, when large cut-off distances are used, large numbers of non-bonded interactions remain inside the cut-off distance.

A second method, which is more commonly used than the first method, also makes use of a cut-off distance. However, the forces beyond the cut-off distance are treated as having a non-zero but constant value. To implement this method, the forces between atoms beyond the cut-off distance are calculated during an initial or set-up step and the sum of these forces that act on each atomic coordinate are saved. Then, in later steps, the previously saved sum of the forces are used for interactions outside the cut-off distance. It has been found that for the same degree of accuracy, that a smaller cut-off distance can be used when the forces beyond the cut-off are treated as constant instead of zero. As such, this second method is less computationally intensive than the first.

Since the movement of atoms during the calculation causes the forces beyond the cut-off distance to slowly change, most implementations of either method periodically recalculate all interactions outside the cut-off distance to update the saved forces. Failure to recalculate a force frequently enough will cause the calculation to be in error. In large molecules, the computer can spend most of its time doing these periodic recalculations. As a result, when performing molecular mechanics calculations to provide a graphical representation of the likely structure of a molecule, it is desirable to do as few recalculations of the forces as possible without reducing the accuracy of the calculation.

SUMMARY OF THE INVENTION

In accordance with the present invention, a computerized molecular modeling system is provided which improves the speed with which a likely structure, representative structure(s), or a sequence of structures of a molecule can be determined and displayed.

In accordance with an embodiment of the present invention, the computerized molecular modeling system determines and displays a structure or structures of a molecule based on the forces used in molecular mechanics calculations, especially molecular mechanics minimizations and molecular dynamics calculations.

In accordance with the system according to the present invention, non-bonded and other interactions which have forces that can be treated as either being approximately constant, or that can be approximated by a rapidly calculated approximation, are not fully recalculated on every iteration. Moreover, in accordance with the present invention, the relative frequency with which the forces associated with different interactions should be fully recalculated is determined, and, using this information, each interaction is fully recalculated only as often as is necessary.

Prior art methods reduce the calculation time of molecular mechanics equations by recalculating the non-bonded interactions between atoms separated by more than a cut-off distance only occasionally. However, to maintain accuracy, each interaction was recalculated before its force changed significantly. Since interactions with the same distance between atoms can greatly differ in their sensitivity to changes in the positions of the atoms, these prior art methods must use a recalculation frequency that is appropriate for the most sensitive of the interactions. Since most interactions are not this sensitive, they are recalculated much more often than is necessary. In addition, the cut-off distance method can not be extended to interactions, such as torsional interactions, that are not functions of distance.

In contrast, in accordance with the present invention, the recalculation frequency is based on each interaction's sensitivity (as defined by a sensitivity factor) to changes in the positions of the atoms. The use of the sensitivity factor to determine recalculation frequencies, instead of a cut-off distance, allows more interactions to be recalculated only occasionally without affecting the accuracy of the calculation. In addition, this sensitivity factor based method can be applied to interactions, like torsional interactions, that can not be effectively treated by the cut-off distance methods. Moreover, it reduces the calculation time by choosing a recalculation frequency for each interaction that is close to its optimal recalculation frequency. In addition, interactions can be assigned to recalculation classes such that interactions having the same or similar recalculation frequency are assigned to the same class.

In accordance with a first embodiment of the present invention, a method for generating an image of a most likely structure, representative structure(s), or a sequence of structures of a molecule is provided as follows:

An initial structure of a molecule is accepted as input into a computer. From the initial structure of the molecule, a total set of interactions is determined which includes subsets of both bonded and non-bonded interactions. The set of bonded interactions comprises several types of interactions, including torsional interactions. An initial total energy for the molecule and an initial total force acting on each atom is calculated from a molecular mechanics energy equation. Note that each interaction generates a force on each of the atoms that comprise the interaction and that each of these forces generally differ in sign and/or magnitude. The total force on each atom is the sum of the forces acting on the atom that are generated by each interaction in the equation that the atom is a part of.

A sensitivity factor for each qualifying interaction of the set of interactions is then calculated based upon its sensitivity to changes in the positions of atoms that make up the interaction. Qualifying interactions are types of interactions that previous experience or testing has indicated might have low sensitivity factors. The types of interactions that can benefit from being treated as qualifying interactions depends on the type of calculation being performed and how much the atoms move on each iteration. However, in virtually all calculations, non-bonded interactions can profitably be treated as qualifying interactions. In situations where the movements are not large, torsional interactions can also be profitably treated as qualifying interactions. In situations where the movements are extremely small virtually all interactions, except possibly bonds, can be profitably treated as qualifying interactions.

Each sensitivity factor indicates a recalculation frequency for its respective qualifying interaction. In addition, interactions with similar recalculation frequencies can be assigned to the same recalculation class, e.g., interactions with recalculation frequencies of 1–4 iterations can be assigned to class A and be recalculated on every iteration; interactions with recalculation frequencies of 5–10 iterations can be assigned to class B and be recalculated on every 5th iteration.

Once the above steps have been performed, an energy minimization procedure (or molecular dynamics procedure) is then performed over a number of cycles. During each cycle, the current force acting on each atom is calculated using the current structure's coordinates and these forces are then used in an algorithm dependent manner to calculate the next structure of the molecule. The next structure is then made the current structure. Each succeeding cycle repeats the process of calculating the forces and using them to calculate the next structure. During each cycle, either the force for each qualifying interaction is fully recalculated from the current coordinates, or the force calculated from a previous cycle is used. Note that in energy minimizations each cycle is typically called an iteration, while in molecular dynamics calculations each cycle is typically called a step. Thus, we will use the terms cycle, iteration, and step interchangeably in this discussion.

The decision to fully recalculate a qualifying force instead of using a previously calculated force depends on when the force was previously calculated and when its respective recalculation frequency indicates that the interaction's previously calculated force is invalid. For example, iteration 1 might be fully recalculated every 5 iterations (recalculation frequency=5), interaction 2 might be fully recalculated every 10 iterations (recalculation frequency=10), and interaction 3 might be fully recalculated on every iteration (recalculation frequency=1). Thus the force for interaction 2 will be calculated on the initial iteration and then fully recalculated only on every 10th succeeding iteration, and the force for interaction 3 will be calculated on every iteration. On all iterations where the force is not fully recalculated, the force is approximated by using the force from the most recent full recalculation.

This process of force calculation and coordinate generation is performed over a number of iterations. In the case of an energy minimization procedure, the iterative process will stop when either the criteria used to indicate that a minimum energy structure has been obtained are met, or some preset maximum number of iterations has been reached. Molecular dynamics calculations typically continue for some preset number of steps.

Finally, the image of the most likely structure, or one or more representative structures of the molecule is generated.

Moreover, in a molecular dynamics calculation, the calculated structures can be displayed in sequence to provide a moving picture of the motion of the molecule in its various conformations or structures.

In accordance with a second embodiment of the present invention, the sum of the forces acting on an atom from all the interactions of a particular class is approximated between full recalculations by a rapidly calculated equation. For example, the sum of the forces acting on an atom due to the interactions in a class that are fully recalculated only every fifth iteration could be approximated between full recalculations by, for example, a quadratic equation. This equation is a function of the number of iterations since the last full recalculation and the coefficients in this equation are calculated using the forces from previous full recalculations.

In accordance with a third embodiment of the present invention, sensitivity classes are incorporated into a Molecular Dynamics (MD) method according to the present invention. The MD method according to the present invention is a predictor-corrector method. In predictor-corrector methods each full step includes substeps. In the first substep, data obtained on previous MD steps is used to calculate the coordinates for the current step. This is called the predictor step. The forces are then calculated using the new coordinates and then these forces, along with those from previous steps are used to make a second, more reliable calculation of the coordinates. This second calculation of the coordinates is called the corrector step. With prior an MD methods it has been found that it is not cost effective to make more than one corrector step for each full step.

The MD method according to the present invention differs from prior art predictor-corrector methods in several ways:

Each full step makes many corrector steps.
  It uses sensitivity classes.
  On each corrector step the forces of only selected classes are recalculated.
  In calculating coordinates for the current step the forces from the next step as well as the forces from the current and previous steps are used.

In accordance with the MD method according to the present invention, the forces acting on each atom are divided into three classes based on their sensitivity:

Bonds, which are the most sensitive interactions.
  A class called Constant, which are interactions whose forces do not significantly as a result of coordinate changes of the size that occur during the refinement of a step's coordinates. The forces due to these interactions are calculated only once on each full step. This class includes most, but not all, non-bonded interactions and most, but not all, torsional interactions.
  A class called Sensitive, which are interactions, like bond angles, that are much less sensitive than bonds but more sensitive than Constant interactions.

Each full step of the MD method according to the present invention includes two substeps, called the extension and refinement substeps, respectively. During the extension substep an estimate of the next step's forces and coordinates is obtained. On the refinement step, the forces from the two previous steps plus the current and next step's forces are used to obtain a reliable estimate of the current steps forces and coordinates. Both the extension and refinement substeps contain several corrector steps. On most corrector steps only the Bond forces are recalculated. The Constant forces are calculated only once per full step and the Sensitive forces are recalculated infrequently.

In accordance with a fourth embodiment of the present invention, the amount of computer memory required to store the information regarding how frequently the forces associated which each non-bonded interaction should be recalculated is reduced through the use of a data compression technique which takes advantage of the characteristics of the recalculation classes.

Atoms in a molecular mechanics calculation are assigned a number and the numbering procedure used in most molecules results in atoms separated by only a few bonds being assigned similar numbers. Since atoms separated by only a few bonds must be in approximately the same region of space, their interactions with other atoms will tend to be assigned to the same one or two recalculation classes.

In accordance with the fourth embodiment of the present invention, each recalculation class has a corresponding bit set. The set has one bit assigned to each interaction of each atom and this bit indicates whether its interaction is a member of the class. Typically if the bit is a 1, the interaction IS a member of the class, and if it is a 0, the interaction is NOT a member.

Since the purpose of providing recalculation classes is to reduce the recalculation frequency as much as possible, in a large molecule all recalculation classes, except for the least frequently calculated class, should have relatively few members. Thus, in large molecules most of the bits in the sets used in conjunction with this embodiment of the present invention should be 0 bits. Moreover, since atoms with similar atomic numbers will tend to be assigned to the same class, the comparatively few 1 bits of each set will be clustered in only a few words of computer memory.

In accordance with a further embodiment of the present invention, a compressed bit set is generated by identifying and saving the words in the bit sets that contain non-zero bits. The words containing only zero bits are discarded. Then, during processing of this compressed bit set, the computerized molecular modeling system knows that any word not identified in the stored list contains only zero bits and acts accordingly.

In accordance with a still further embodiment of the present invention, additional memory space is saved by recording each interact/on once, namely as an interaction between a lower numbered atom and a higher numbered atom. Thus, for example, the interaction between atoms 2 and 5 will be recorded as an interaction between atom 2 and atom 5. The fact that atom 5 has an interaction w separately. Note that since the 1-2 and 2-2 interactions are not recorded as one of atom 2's interactions, the 2-3 interaction is atom 2's first interaction and the 2-5 interaction is its third interaction.

BRIEF DESCRIPTION OF THE DRAWINGS

FIG. 3 is an illustrative energy equation.

DETAILED DESCRIPTION OF THE INVENTION

Figure 1:
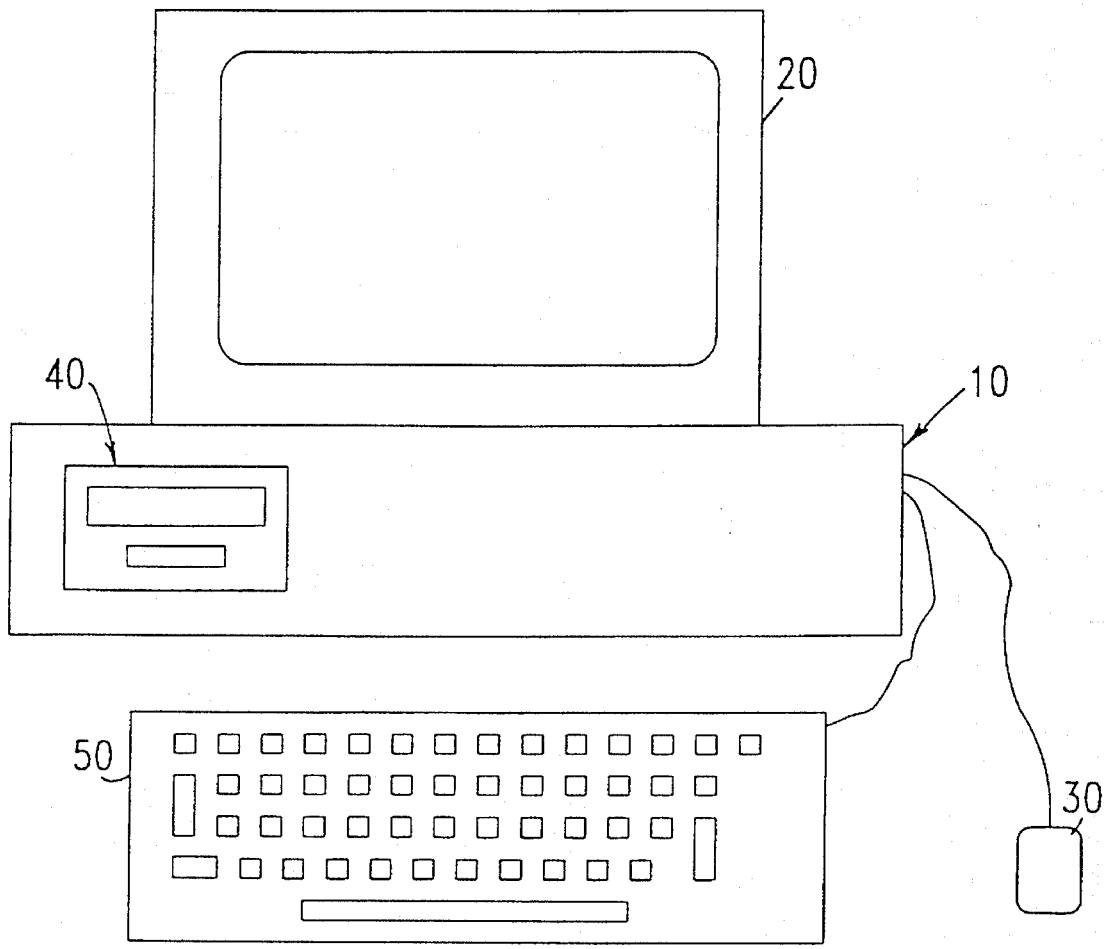
FIG. 1 shows a computerized molecular modeling system according to the present invention.

Referring to FIG. 1, a computerized molecular modeling system 1 according to an embodiment of the present invention includes a-computer 10 coupled to a display terminal 20, a mouse 30, a keyboard 50, and an external storage device 40.

In accordance with an illustrative embodiment of the present invention, a user can operate the system 1 to create graphical displays of molecules and to perform energy minimizations or molecular dynamics techniques to determine and display a most likely structure, representative structure(s) or a sequence of structures of a molecule or aggregate of molecules. As explained above, each of these techniques involves repeatedly calculating the resultant force and displacing various atoms in order to identify the most likely structure, representative structure(s) or a sequence of structures of the molecule. In accordance with the present invention, the processing time used by computerized molecular modeling systems in order to identify the most likely structure, representative structure(s) or a sequence of structures of the molecule is reduced by utilizing a sensitivity factor to determine the frequency with which various interactions must be calculated during the molecular mechanics calculations.

In accordance with an illustrative embodiment of the present invention, the mouse 30 can be used in conjunction with the keyboard 50 to create an initial structure for a molecule or aggregate of molecules. This initial structure may be graphically illustrated on the display terminal in a variety of formats. For example, the molecule can be illustrated in a stick and ball format (FIGS. 5a–d), or a volume format. The display can also simulate a 3 dimensional view of the molecule. Moreover, the molecule can be rotated so that the user can examine the molecule's structure from various viewpoints.

Figure 2B:
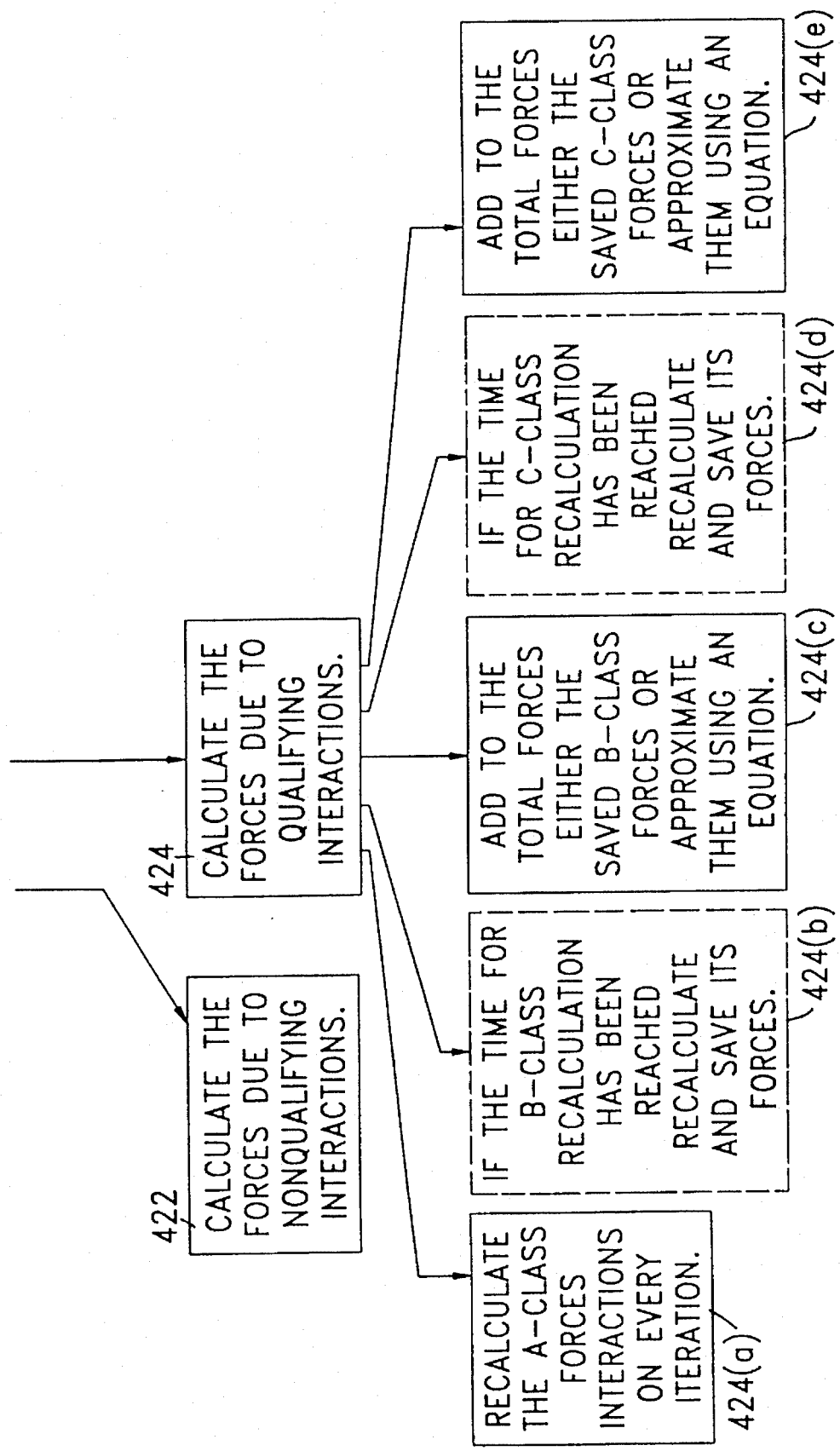
FIG. 2 is illustrates a process flow for a computerized molecular modeling system in accordance with the present invention.

Referring to FIG. 2, the computerized molecular modeling system in accordance with the present invention may operate as follows:

Control information and the initial structure of the molecule or aggregate of molecules is obtained from the user (100, 200). Examples of control information include: how many iterations are to be done; what information is to be saved or displayed about the initial, intermediate, and final structures; and which energy equation is to be used. FIGS. 5(a–d), which will be discussed in more depth below, illustrate sets of initial coordinates for various structures of an ethane molecule and their respective graphical representations in stick and ball format. From this structure and control information, the system generates a set of interactions. Each atom has one or more interactions with each other atom, and each interaction produces forces that act on each of its atoms. Many interactions involve only two atoms, but some, for example, involve three or four atoms. In general, an interaction generates a different force on each of its atoms.

Parameters are assigned to each interaction based on the particular force field being used for the procedure. All terms in the energy equation that are neither numeric constants nor geometric factors calculated from the structure are called parameters. All the parameters for each interaction in the energy equation must be supplied before the calculation can be performed.

The initial energy (E) and the initial forces are then calculated for each interaction (300). A sensitivity factor as described below may be calculated for qualifying interactions (310). Each interaction for which a sensitivity factor is calculated is assigned a recalculation frequency based on its sensitivity factor. As explained below, each interaction may be further assigned to one of several recalculation classes based on its recalculation frequency.

Once the above procedures are performed, the system begins to perform energy minimization techniques (or molecular dynamics)(400). Using the force (and momentum in the case of molecular dynamics), the atoms are moved from their initial coordinates (410) to a new set of coordinates. Several methods for both minimizations and molecular dynamics calculations using the forces to generate new coordinates are known to those skilled in the art. Such methods are discussed, for example, in the following articles: Burkert, U. and Allinger, N. L., "Molecular Mechanics ACS Monograph 177", American Chemical Society, (1982) and Haile, J. M. "Molecular Dynamics Simulations, Elementary Methods", John Wiley (1992). Once the new coordinates are determined, the force must be recalculated using the new coordinates (420). This process is repeated for a number of iterations using known techniques in order to find, in the case of minimizations, a minimum energy of the molecule.

In accordance with the present invention, however, the force is not fully recalculated for each interaction every time the forces of a new structure are calculated. Interactions whose forces are highly sensitive to changes in coordinates are fully recalculated on each iteration (422). However, less sensitive interactions, especially non-bonded interactions, are fully recalculated only as often as their respective recalculation frequency indicates. If recalculation classes are used, then all interactions in the first recalculation class, which might include all interactions with recalculation frequencies of 1–4, would be fully calculated on every iteration (424(a)). Interactions in the second recalculation class, which might include all interactions with recalculation frequencies 5–9, would be fully calculated only on every 5th iteration (424(b,c)) and so on (424(d"e)). Forces not fully recalculated on every iteration are either treated as being constant between recalculations or are approximated using a rapidly calculated equation. Moreover, the recalculation classes themselves are reassigned periodically (430) because, as the atoms move, an interaction's sensitivity factor may change. As such, the sensitivity factors are recalculated periodically and the interactions reassigned to the recalculation classes.

Each iteration, or once every few iterations, the new coordinates of the atoms may be plotted on the display terminal and the energy of the molecule at these coordinates can be displayed to the user (440, 500). Illustrative displays, in accordance with the present invention, are shown for various views and conformations of an ethane molecule in FIG. 5(a–d). This process continues, in the case of minimizations, until a minimum energy structure of the molecule is found. Once a minimum energy structure is found, it is plotted on the display terminal as the likely structure of the molecule along with its calculated minimum energy.

A. Discussion of the Relevant Chemical Principles

In order to more fully explain the present invention, a quick review of some of the relevant chemical principles is useful.

As explained above, it is generally accepted that the most accurate and reliable method for determining the structure and properties of molecules is complete quantum mechanics done without using approximations. Unfortunately the amount of computer time required to do such a calculation increases as the 4th power of molecular size and significant amounts of computer time are required to do even a single energy or force calculation for a small molecule. Thus, complete quantum mechanics calculations are usually confined to molecules with fewer than 20 nonhydrogen atoms. For larger molecules, either approximate quantum mechanics methods are used, which reduce the reliability of the calculation, or less expensive methods, such as molecular mechanics, are used.

Molecular mechanics calculations are much faster and cheaper than complete quantum mechanics calculations. Moreover, when used properly, molecular mechanics calculations can approach the accuracy of complete quantum mechanics calculations. Thus they are often the best calculation method for medium sized molecules and are usually the only practical method for large molecules or aggregates of molecules. The basic assumption of molecular mechanics is that the essential features of a quantum mechanics calculation can be approximated by classical mechanics. These features are captured in an energy equation and in a set of adjustable parameters that is used in conjunction with the equation.

A particular energy equation-parameter combination is known as a force field. A number of different force fields have been proposed and several of these are widely used. Examples of widely used force fields are the MM2 and MM3 force fields, which were developed by Allinger and coworkers as set forth in the following publications: Allinger, N. L. *Journal of the American Chemical Society*, 1977, Volume 99, page 8127 and Allinger, N. L.; Rahman, M.; Lii, J. -H., *Journal of the American Chemical Society*, 1990, Volume 112, page 8293; the AMBER force field, which was developed by Kollman and coworkers as set forth in the following publications: Weiner, S. J; Kollman, P. A.; Case, D. A.; Singh, U. C.; Ghio, C.; Alagoma, G. Profeta, S.; and Weiner, P., .*Journal of the American Chemical Society*, 1984, Volume 106, page 765; and the SYBYL force field, which is distributed by Tripos Associates as discussed in Clarke, M.; Crammer, R. D.; and Van Opdenbosh, N., *Journal of Computational Chemistry*, 1989, Volume 8, Page 982.

Force fields may differ in several ways:

They can contain different interactions. For example, the MM2 and MM3 force fields contain a combination bond stretching—bond angle bending interactions that are not present in the other force fields mentioned above.

They can use different functions to calculate the same interaction. For example, the MM2 and MM3 force fields use a 6-exponential function to reproduce van der Waals interactions while most force fields use a 6–12 function similar to the one shown in FIG. 3.

They can use different parameters. For example, virtually all force fields use a quadratic function for bond angles, however, the two parameters used in the function, the k and 1° terms, are generally different in different force fields.

Despite these differences, widely used force fields usually give qualitatively similar results when applied to the same molecule. Since each force field is trying to reproduce what occurs experimentally, this similarity in results is not surprising.

FIG. 3 shows a representative molecular mechanics energy equation. This equation contains terms that can be found in many force fields. However, the energy equations used in the force fields mentioned above differ to a greater or lesser extent both from each other and from the equation in FIG. 3.

Even when the equation for an interaction is the same, different force fields generally use different parameters for the same interaction. Since calculating the typical molecule requires many different parameters and each parameter must be determined by a time consuming, empirical process, the parameters necessary to calculate a particular molecule may not be available in all force fields. In practice, the availability and reliability of the parameters used in a force field are more important than the energy equation in determining how suitable it is for calculating a particular molecule.

Two different types of Molecular Mechanics calculations can be performed:

Energy minimizations

Molecular dynamics

In energy minimizations, an algorithm is used to vary the position of each atom until a minimum in the energy of the molecule, as determined by the force field, is found. This static, minimum energy structure is then taken to represent what occurs in an experiment. This corresponds to doing an experiment in a vacuum at absolute zero. While very few experiments are performed under these conditions, it has been found that the time averaged structure of a molecule in a particular conformation is usually similar to the conformation's minimum energy structure.

The most widely used methods for minimizing the energy are the steepest descent method, the Newton-Raphson method, and conjugate gradient methods. Combinations and variants of these methods are also used. The present invention, however, is applicable to each of these molecular mechanics minimization methods.

Each of these minimization methods iteratively apply a two step process. Once each iteration, the force on each atom is calculated. In the Newton-Raphson method, the forces and the derivatives of the forces are also calculated. Then the forces (plus their derivatives in the case of the Newton-Raphson methods) are used in an algorithm dependent manner to move each atom in the direction that reduces the energy of the molecule. This two step process is then repeated until conditions are met which indicate that the energy of the molecule has been minimized. Typically, minimizing a molecule requires from 10 to 10,000 iterations.

Figure 5A:
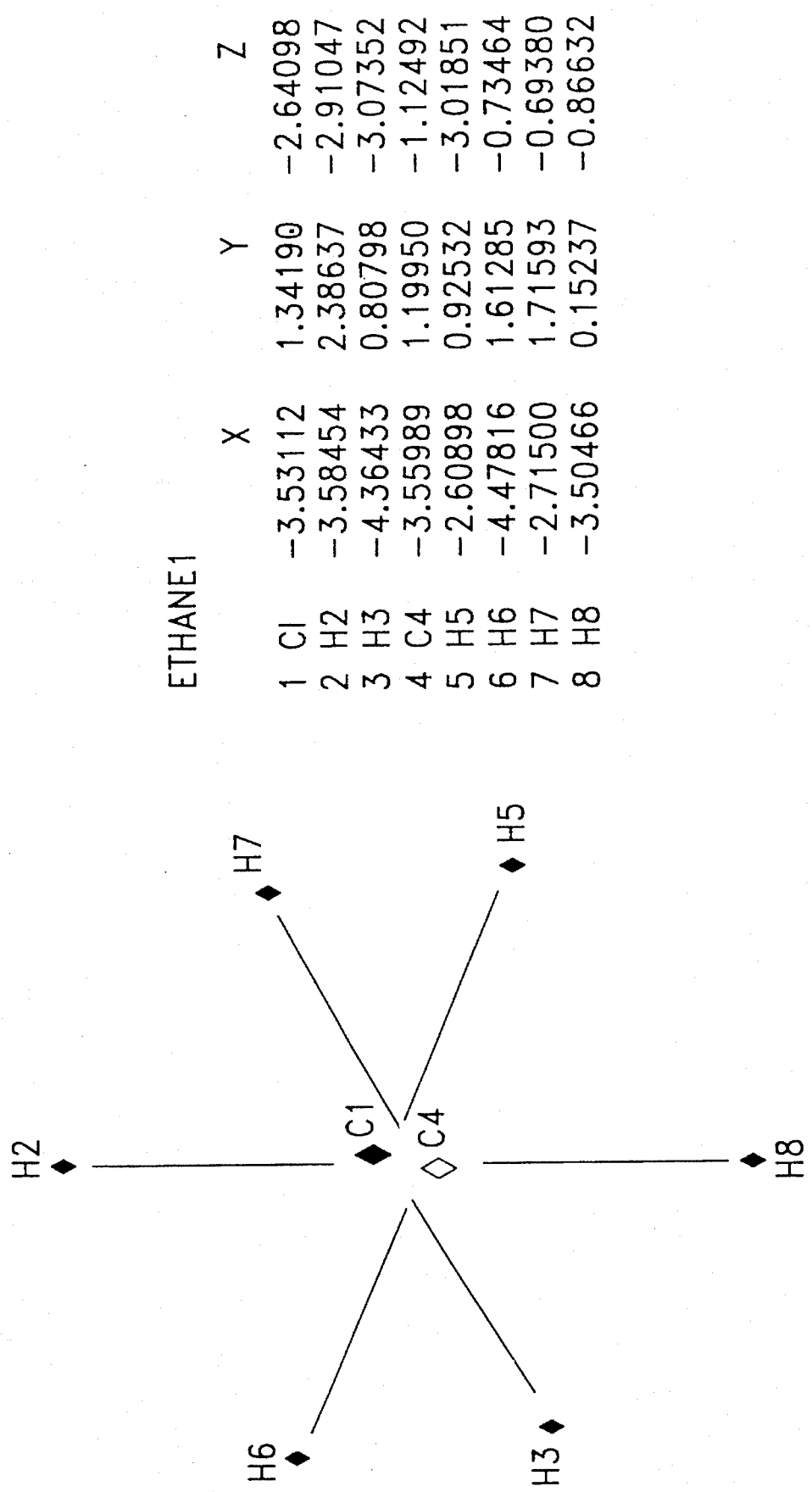
FIG. 5a shows a ball and stick model of the staggered conformation of an ethane molecule viewed down its central bond (C1–C4).
Figure 5B:
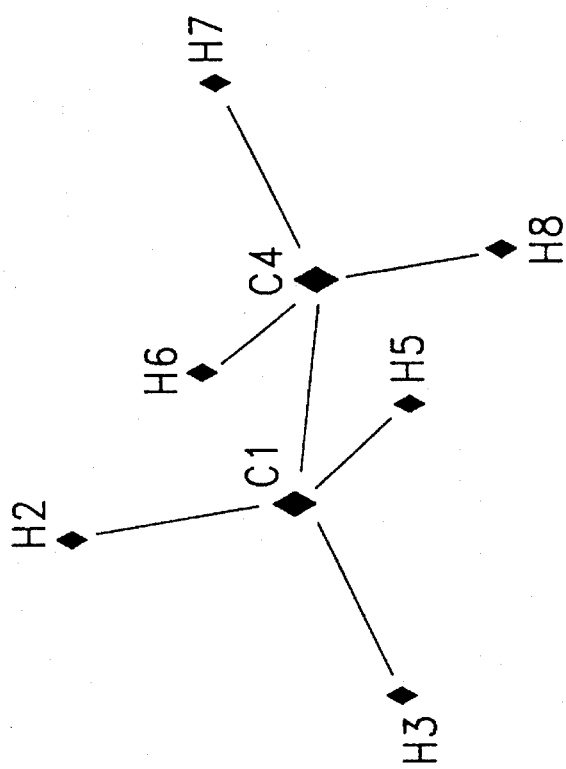
FIG. 5b shows a ball and stick model of the staggered conformation of the ethane molecule viewed at an angle to the central bond.
Figure 5C:
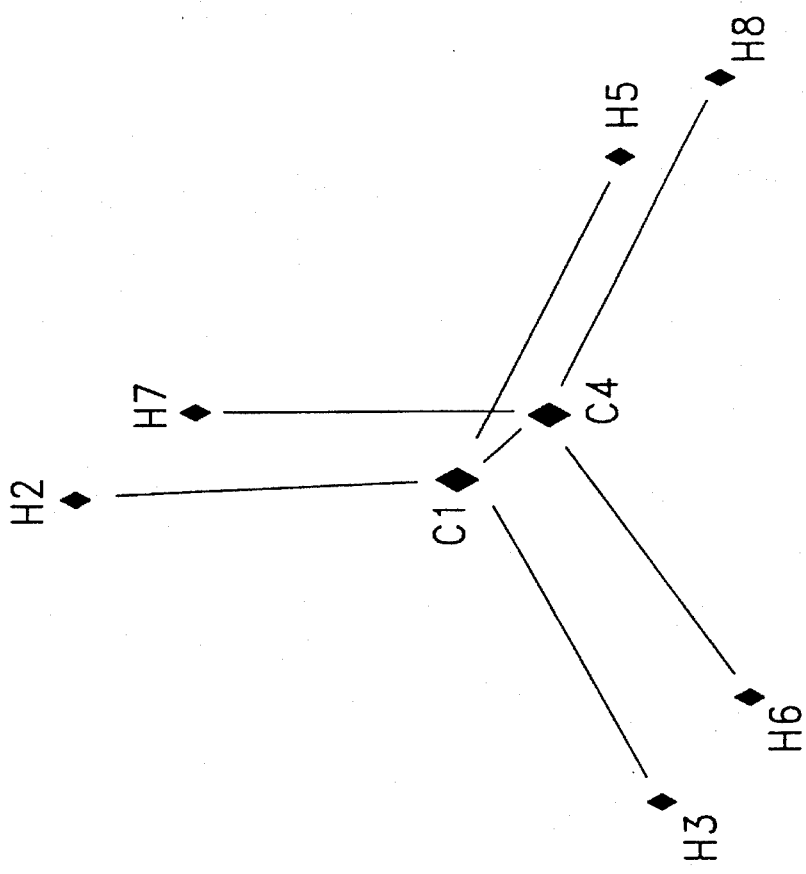
FIG. 5c shows a ball and stick model of the eclipsed conformation of the ethane molecule viewed down its central bond (C1–C4).
Figure 5D:
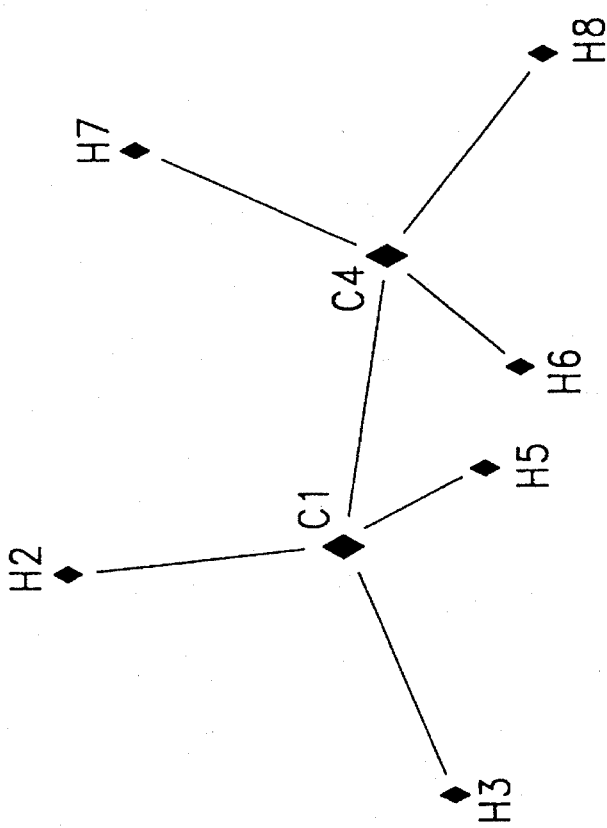
FIG. 5d shows a ball and stick model of the eclipsed conformation of the ethane molecule viewed at an angle to the central bond.

A major limitation of minimization techniques is that the typical molecule has many minima. There is one minima for each of the molecule's conformations. Different conformations of a molecule have the same bonds, bond angles and other interactions but the location of the atoms relative to each other is different. When a molecule changes its conformation it changes in a way that is analogous to the way a jackknife changes when it is opened or folded. FIG. 5(a) and 5(b) show two views of a "staggered" conformation of an ethane molecule, along with the coordinates of the atoms in the molecule. The coordinates shown are "external" coordinates. In other words, the coordinates are taken from the viewpoint of the observer. As such, even though the coordinates shown are different for the two different views, the "internal" coordinates, i.e., the distance between atoms, or the coordinates of the atoms with respect to each other, are the same for both views. The energy equation of FIG. 3 uses "internal" coordinates. As such, the particular "view" chosen by the user of the molecular modeling system according to the present invention for the initial coordinates of the atoms will not affect the calculations. FIGS. 5(c) and 5(d) illustrate two views of an "eclipsed" conformation of an ethane molecule. As such, while the internal coordinates (not shown) of FIGS. 5(c) and 5(d) are the same, these internal coordinates are different from the internal coordinates for FIGS. 5(a) and 5(b).

As such, since the shape and energy of a molecule varies with its conformation, the calculated results will agree with experimental data only if the conformation used in the calculation corresponds to the conformation found experimentally. Usually the experimental conformation is the one with the lowest energy. Unfortunately, minimization techniques find only the minimum that is closest to the initial structure supplied by the chemist. To find the lowest energy conformation, the chemist must supply initial structures that are close to each of the possible conformations, minimize the energy of each initial structure and then compare the energies of the minimized structures to determine which has the lowest energy. Finding and minimizing all chemically reasonable initial structures can be very time consuming, so time consuming that it is impossible to find and minimize all the conformations of a large molecule like a protein.

Another limitation of minimizations is that they ignore entropy effects. Since entropy is an important part of many phenomena, those of skill in the art will appreciate that this is a significant limitation.

Molecular mechanics force fields can also be used to do molecular dynamics. Molecular dynamics calculations integrate Newton's second law of motion to reproduce the movement over time of the atoms in both single molecules and in aggregates containing many molecules. The advantage of molecular dynamics is that it reproduces the dynamic nature of molecules under experimental conditions. For example, if there are many minima, a molecule will visit all of them during a properly conducted molecular dynamics calculation and the calculated properties will be a statistical average of all the minima—just as the experimental results are a statistical average.

A statistical average of all minima is useful because it is not unusual for the statistical average to differ from the minimum energy structure. The four most common reasons for such differences are:

(1) The molecule has many conformations with energies only slightly higher than the lowest energy conformation. As a result, the lowest energy conformation occurs only slightly more frequently than the other conformations. Given the large number of other conformations, this means that the molecule spends most of its time in conformations other than the lowest one.

(2) The molecule spends almost all its time in the minimum energy conformation but the potential energy well around the conformation's minimum energy structure is very unsymmetrical. At a result of this asymmetry, the conformation's average structure is significantly different from its minimum energy structure.

(3) Entropy effects cause higher energy conformations to occur more frequently in the experimental sample than the minimum energy conformations. The frequency with which a minima occurs depends on its free energy and the free energy is determine by both the energy and the entropy. Usually the largest component of the free energy is the energy and as a result variations in the free energy are usually dominated variations in the energy. However, when the contribution of the entropy is large, entropy effects can be more important than the energy in determining the free energy. (Texts on thermodynamics should be consulted for a discussion of the difference between the energy and free energy.)

(4) The Chemist doing the calculation has not done an extensive enough search for the minimum energy conformation and the conformation he or she thinks is the lowest energy conformation is in fact a higher energy conformations. Given the immense number of possible conformations in medium or large molecules, it is often impossible for the chemist to calculate all of them and thus be certain the one with the lowest energy has been identified.

The two most widely used molecular dynamics integration procedures are the Grear method and the Verlet method. (A discussion and comparison molecular dynamics methods can be found in Haile, J. M "Molecular Dynamics Simulations, Elementary Methods", John Wiley (1992).) Both methods reproduce how an initial structure changes with time by calculating the sequence of structures that occur at evenly spaced time intervals. On each iteration, both methods recalculate the forces acting on the current structure and then uses these forces to calculate how the structure changes over a short period of time. The changes are then applied to the current structure to produce the next structure in the sequence. The next structure is then made the current structure and the process is repeated. Where the methods differ is in the algorithm used to calculate the changes. The time interval between structures is known as the time step and is typically on the order of $10^{-14}$ to $10^{-16}$ seconds. A typical molecular dynamics calculation will simulate $10^{-12}$ to $10^{-8}$ seconds, which means that it consists of 100 to 100,000,000 force and structure recalculations.

Chemists use the results of molecular mechanics calculations in a variety of ways. These calculations can be used, for example, as a method for determining the structures and thermodynamic properties of a molecule or a group of molecules and then drawing conclusions based on these properties. For instance, given a set of possible drug molecules, it is possible to calculate their binding energy with a protein and then synthesize and test only those drug molecules with favorable binding energies. (The binding energy is the change in the total energy, protein+molecule, that occurs when a molecule binds to the protein.)

Force calculations are central to both minimizations and molecular dynamics.

Forces are central to minimizations because the mathematical definition of a minimum is:

$$F_i = 0, \text{ for all } i \tag{1}$$

Where $F_i$ is the force on atom i.

In accordance with this equation, when a system is at a minimum the net force on all atoms is zero.

Forces are also central to molecular dynamics because such calculations are integrations of Newton's second law of motion, which can be written as:

$$F_i = m \partial v_i / \partial t \tag{2}$$

Where $v_i$ is the velocity of an atom.

In accordance with this equation, the rate of change in an object's momentum (the acceleration) is proportional to the force acting on it.

The force acting on an object in some arbitrary direction, labeled $X_i$, is defined as:

$$F_i = -\partial E/\partial X_i \tag{3}$$

Where $\partial$ is the symbol for partial differentiation, E is the energy, $F_i$ is the force in the $X_i$ direction.

Because of the above relationship between the force and the derivative of the energy, these two terms may be used interchangeably in the context of the present invention.

All widely used force fields contain terms for non-bonded interactions. In virtually all force fields there is a non-bonded interaction term for all pairs of atoms that are not part of the same bond, or bond angle. In a large molecule the number of non-bonded interactions is quite large. If n is the number of atoms, there are approximately $n^2/2$ non-bonded interactions. This means that when n is large, the energy equation for the molecule contains many more non-bonded interactions than all other interactions combined. For example, a 30 atom molecule will usually have over 800 non-bonded interactions but only about 30 bonds, 60 bond angles and 90 torsional angles. In a large molecule, one with several thousand atoms, both the number of non-bonded interactions and their predominance compared to other interactions is even greater.

The large number of terms that need to be evaluated causes minimizations and molecular dynamics calculations of large molecule to take hours or even days on even the fastest computers. Thus while molecular mechanics calculations are less expensive than quantum mechanics calculations, they can still be time consuming and expensive.

Given the cost and delay involved in doing calculations of large molecules or large aggregates of molecules, a need arose to reduce the computer time required for these calculations. Since most of the computer time is spent calculating non-bonded interactions, these interactions have received the most attention.

As set forth above, two methods have been widely used in both minimizations and molecular dynamics calculations to reduce the time spent calculating non-bonded interactions:

The first method takes advantage of the fact that forces between widely separated atoms are small. This method establishes a distance, known as the cut-off distance, and all forces between atoms separated by distances greater than the cut-off distance are assumed to be zero and not calculated. Since the atoms move during the calculation, atoms can move in either direction across the cut-off distance. Thus most implementations of this method periodically redetermine which atoms are beyond the cut-off distance.

The second method also makes use of a cut-off distance, but treats the forces beyond the cut-off distance as having a non-zero but constant value. Since the movement of atoms during the calculation causes the forces beyond the cut-off distance to slowly change, most implementations of the second method periodically recalculate all interactions outside the cut-off distance to update the saved forces.

For such occasional recalculations to work, each interaction must be recalculated before its force changes significantly. However, as stated above, interactions with the same distance can vary greatly in their sensitivity to changes in the positions of the atoms. To ensure that all interactions are recalculated frequently enough, the current, distance based methods must use a recalculation frequency that is appropriate for the most sensitive interactions. Since most interactions are not this sensitive, they are recalculated more often than is necessary.

B. The Molecular Modeling System According to the Present Invention

In accordance with the present invention, the recalculation frequency is based on an estimate of each interaction's sensitivity (as defined by a sensitivity factor) to changes in the distance between the atoms. The use of sensitivity factors to determine recalculation frequencies instead of a cut-off distance has two benefits:

It allows more interactions to be recalculated only occasionally without affecting the accuracy of the calculation.

It provides a reduction in the calculation time by choosing a recalculation frequency for each interaction that is close its optimal recalculation frequency.

In accordance with the present invention, a sensitivity factor ($S_{nb}$), which captures the sensitivity of a non-bonded force to changes in the distance, is defined as the derivative of the force with respect to the distance:

$$S_{nb} = |\partial F_{nb}/\partial R_{nb}| \tag{4}$$

Where S is called the sensitivity factor, the $||$ symbol indicates that we want the scalar size of the derivative, and $F_{nb}$ and $R_{nb}$ are the force and distance, respectively, between two atoms involved in a particular non-bonded interaction.

The sensitivity factor is set equal to the scalar size of the derivative because the magnitude of the change in the force with respect to distance is of interest, not whether this change is positive or negative.

The derivative can be calculated either numerically or analytically. The numerical calculation is done by moving the atoms and recalculating both the force and the distance. The change in the force is then divided by the change in the distance.

$$S_{nb} = |\Delta F_{numeric}/\Delta R_{numeric}| \tag{4a}$$

Where $\Delta F_{numeric}/\Delta R_{numeric}$ are the change in the force and the distance, respectively, that occurs when the atoms are moved.

Under conditions where the change in the coordinates is approximately the same for all interactions, $|\Delta F_{numeric}|$ can be used instead of $S_{nb}$ to assign interactions to sensitivity classes. One could also calculate $|\Delta F_{numeric}|$ by varying $R_{nb}$ directly, without varying the coordinates that determine $R_{nb}$, and then recalculating the force.

The analytical differentiation can be done by making use of the following equation:

$$F_{nb-i} = -\nabla E_{nb-i} \tag{4b}$$

Where i stands for an atom and $\nabla$ is the symbol for vector differentiation, and when Cartesian coordinates are used it is equal to:

$$\nabla = (\partial/\partial x_i)i + (\partial/\partial y_i)j + (\partial/\partial z_i)k \tag{4c}$$

Where $x_i$, $Y_i$, and $z_i$ are the coordinates of one of the two involved in the interaction and i, j, and k are the unit vectors in the X, Y, and Z directions, respectively. (Note that changing the atom used in the differentiation changes the sign but not the magnitude of $\nabla E_{nb}$ for the non-bonded interactions in the energy equation in FIG. 3.)

Given the relationship between the force and the energy, equation (3), equation (4) can be rewritten as:

$$S_{nb} = |\partial(\nabla E_{nb}/\partial R_{nb}| \tag{5}$$

For the non-bonded interaction between atoms i and j in the non-bonded portion of the energy equation in FIG. 3, equation (5) can be written as:

$$S_{i,j}=Abs[3q_iq_j/R^3_{i,j}+48A_{i,j}R^{o6}_{i,j}/R^8_{i,j}+168B_{i,j}R^{o12}_{i,j}/R^{14}_{i,j}] \quad (6)$$

Where $R_{i,j}$ is the distance between the two atoms, $q_i$ and $q_j$ are the partial charges on each atom, $A_{i,j}$ is the coefficient for the van der Walls interaction's attractive term, $B_{i,j}$ is the coefficient for the van der Waals interaction's repulsive term, and $R°$ is the van der Waals radius for the interaction.

It should be noted, however, that equation (6) is generally applicable only for the non-bonded portion of the energy function given in FIG. 3. Some force fields use a different energy function and this results in a different equation for the sensitivity factor. To obtain the equation for the sensitivity factor for non-bonded energy functions different from the one in FIG. 3, equation (5) applies and the indicated differentiation must be performed. This differentiation can be performed using techniques taught in Calculus courses or by using a program that performs symbolic differentiation. Examples of programs that perform symbolic differentiation are the Derive™ program, which is distributed by Soft Warehouse, Inc. and the Mathematica™ program, which is distributed by Wolfram Research, Inc.

While any interaction identified by the sensitivity factor (equation (5)) as being sensitive should be recalculated frequently, there are at least two special cases where more frequent recalculations are needed than the sensitivity factor alone would indicate.

For example, when the distance between the atoms is close to $R°$ and the values of $q_i \cdot q_j$, $A_{i,j}$, and $B_{i,j}$ are all small, both the force and the sensitivity factor are small. However, the interaction is also close to the point where it becomes dominated by the repulsive $R^{o12}/R^{14}$ term of the equation. Under these conditions, relatively small movements of the atoms towards each other results in a large increase in both the interaction's force and its sensitivity factor.

Figure 7:
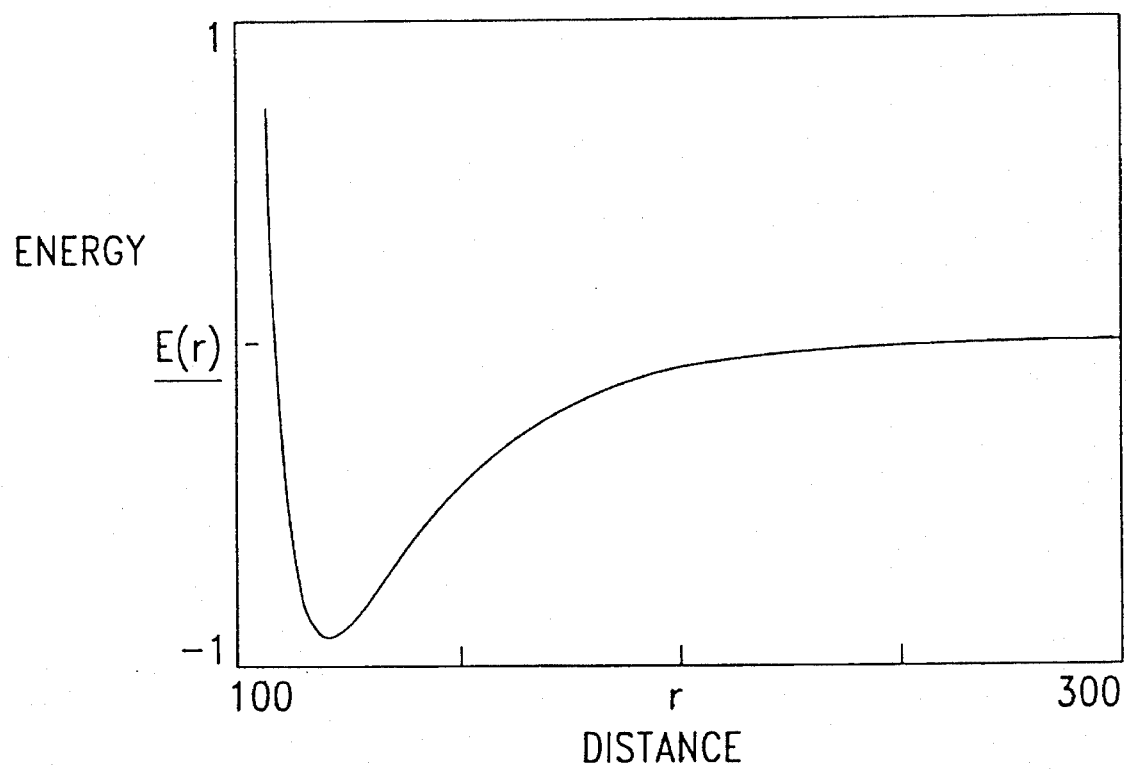
FIG. 7 illustrates a non-bonded interaction energy curve with an inflection point.

A second special case arises near an inflection point of the interaction. An inflection point is the point on a curve where the second derivative, also known as the curvature of the function, goes through zero as it changes from positive to negative. Most non-bonded interactions have one or more inflection points. FIG. 7 illustrates the qualitative features of many non-bonded interactions. Note that the curvature of the function is positive at the minimum but its asymptotic approach to zero can occur only if the curvature is negative for some part of the curve. Since the second derivative of the energy is a continuous function, this means there must be an inflection point, where the second derivative of the energy changes from positive to negative.

What both special cases have in common is that the derivative of the sensitivity factor, S, with respect to distance has a significant value even though S is small. The two special cases described above could be accommodated if equation (5) is modified as follows to include both the first and second derivatives of the force to calculate the sensitivity factor:

$$S_{nb}=|\partial F_{nb}/\partial R_{nb}|+|\partial^2 F_{nb}/\partial R_{nb}^2 \cdot \Delta R_{nb}| \quad (7)$$

Where $\Delta R_{nb}$ is the likely change in the distance between the atoms before the next recalculation of the force.

Another way to ensure that all forces are recalculated frequently enough is to recognize that the above special cases occur at predictable places along the non-bonded energy-distance curve and use a combination of the sensitivity factor and the distance between the atoms to determine the recalculation frequency. For example, when the distance is close to $R°$ or smaller, the interaction could be assigned to the class that is recalculated most frequently, even if the sensitivity factor indicated it could be recalculated less frequently. Similarly, the interaction could be assigned to the class that is recalculated with a moderate frequency if, for example, the distance was less than $2R°$ but greater than $R°$ even if the sensitivity factor indicated it could be recalculated less frequently. Of course, both equation (7) and distance limits could be used to provide a particularly reliable result.

In accordance with the present invention, recalculation frequencies can be derived from the sensitivity factor in several ways. One way is to empirically determine an optimum recalculation frequency for various values of the sensitivity factor. The following pseudo FORTRAN code illustrates the use of an empirical combination of an interaction's sensitivity factor and its $R°$ value to assign an interaction to a recalculation frequency class:

```
IF ((SIJ.LT.0.001).AND.(RIJ.GT.2.0 * R0(I,J)) THEN
    N_C_CLASS = N_C_CLASS + 1
    C_CLASS_LIST (N_C_CLASS) = N_NBD
ELSE IF ((SIJ.LT. 0.05).AND.(RIJ.GT. R0(I,J)) THEN
    N_B_CLASS = N_B_CLASS + 1
    B_CLASS_LIST (N_B_CLASS) = N_NBD
ELSE
    N_A_CLASS = N_A_CLASS + 1
    A_CLASS_LIST (N_A_CLASS) = N_NBD
END IF
```

In the above pseudo code, I and J are the atoms involved in the interaction, SIJ is the interaction's sensitivity factor, which was calculated using equation (6), RIJ is the distance between them, and R0(I,J) is the interaction's van der Waals $R°$ value, N_C_CLASS, N_B_CLASS, and N_A_CLASS keep track of the numbers of interactions in the A, B, and C classes, respectively, and N_NBD is a running count of the number of non-bonded interactions encountered so far (each interaction has a unique value of N_NBD associated with it).

The conditions used in this pseudo code were found by trying various combinations of the sensitivity factor and $R°$ until a combination was found that substantially reduced the time required to calculate the non-bonded forces and yet gave essentially the same results as a calculation where all the forces were recalculated on every iteration, as measured by the change in the total energy during a 0.1 picosecond molecular dynamics simulation at 600K with step sizes of about $2 \times 10^{-15}$ seconds. This testing was done using a force field based on the energy equation in FIG. 6, the velocity form of the Verlet algorithm (Swope, et at, *J. Chem. Phys*, Vol 76, p648, 1982), and a 34 atom molecule that had no hydrogen atoms. As will be discussed below, the recalculation frequencies are more generally a function of both the sensitivity factor and the amount the atoms move on each step. Thus, a more general set of assignment code can be produced by incorporating into the code above either the amount each atom moves during each step or using factors, such at the atomic mass, the temperature, etc., that effect the amount atoms move, or using criteria that were conservative enough to handle all reasonable situations.

Another way to use the sensitivity factor to determine recalculation frequencies is make use of equation (8):

$$n_{i,j}=f/S_{i,j} \quad (8)$$

Where $n_{i,j}$ is the recalculation frequency for the interaction between i and j, and f is an empirically determined factor.

If equation (8) is used, it is likely that the optimum value of f will vary with the calculation being done. For example, if a larger time step or a higher temperature is used in a molecular dynamics calculation, the atoms move further on each iteration. For any particular value of $S_{i,j}$, larger atom movements on each iteration should result in fewer iterations between recalculations. Thus, the value of f used should either be small enough the insure that interactions are recalculated frequently enough even under all reasonable circumstances, or the value of f used should vary with the conditions.

Another way to use the sensitivity factor to determine the recalculation frequency is to make use of the Taylor's series expansion and rearrange:

$$\Delta F_{max} = S_{i,j} \cdot \Delta R_{i,j} \tag{9}$$

$$\Delta F_{max} = S_{i,j} \cdot \Delta l_{i,j} \cdot n_{i,j} \tag{10}$$

$$n_{i,j} = \Delta F_{max}/(S_{i,j} \cdot \Delta l_{i,j}) \tag{11}$$

In the above equations, $\Delta F_{max}$ is the maximum amount a force can change without significantly affecting the accuracy of the calculation, $n_{i,j}$ is the recalculation frequency for the i-j interaction, $\Delta R_{i,j}$ is the amount the distance between the atoms changes between recalculations, and $\Delta l_{i,j}$ is the amount the i-j distance changes on one iteration. Note that $S_{i,j}$ can be calculated using either equation (4) or equation (7).

The value of $\Delta l_{i,j}$ can be obtained in several ways. For example, it can be determined empirically by trying different values on test calculations until a value that works reliably is found. Alternatively, the value of $\Delta l_{i,j}$ can be monitored during the course of the calculation and the most recent value of $\Delta l_{i,j}$ can be used to estimate the recalculation frequency. Moreover, when the velocity of the atoms is known, as is usually the case in a molecular dynamics calculation, this velocity can be used to estimate $\Delta l_{i,j}$ for the next iteration.

For molecular dynamics calculations the value of $\Delta l_{i,j}$ used has to take into account the fact that the velocity of each atom changes rapidly. This change occurs because the atoms oscillate with a frequency on the order of $10^{-14}$ seconds. During each oscillation an atom's velocity changes from a positive value through zero to a negative value and then back again. Thus if the simulated time between recalculation is of the same order as the oscillation frequency, it is better to use the average speed of atoms i and j, where the average is taken over at least one full oscillation. The average speed can be calculated in the usual manner from the velocity. Each atom's average speed can also be approximated by periodically calculating the average instantaneous speed of all the atoms in the molecule and then adjusting this average for the mass of the particular atom one is interested in.

The oscillatory nature of atomic movements also means that when the time between recalculations is much longer than the oscillation frequency that the average value of $\Delta l_{i,j}$ will be greatly over estimated if it is calculated using either the current velocity or the average speed. One can deal with this over estimate in several ways. One could ignore this fact in order to be sure that the interactions were recalculated frequently enough, or one could reduce the calculated value of $\Delta l_{i,j}$ by an empirically determined factor, or one could monitor the net movement over one or more recalculation cycles in order to obtain an estimate of the average value of $\Delta l_{i,j}$ between full recalculations of the forces.

Once the sensitivity factor, $S_{i,j}$ and $\Delta l_{i,j}$ has been determined, the i-j interaction can be assigned to a recalculation frequency class in two different ways. One way is the use equation (11) and assign it to the class whose recalculation frequency is closest to but still smaller than $n_{i,j}$. Alternatively, one can use equation (10) and calculate the interaction's $\Delta F_{max}$ for each class by replacing $n_{i,j}$ with each class's recalculation frequency. The interaction is then assigned to the class with the largest recalculation frequency for which the calculated $\Delta F_{max}$ is less than the $\Delta F_{max}$ for that class.

The value of $\Delta F_{max}$ in equations (9) through (11) can be determined empirically by trying different values in test calculations until a value is obtained that works reliably. It has been found that the optimum value of $\Delta F_{max}$ depends on the details of the calculation in which it is employed. For example, in molecular dynamics calculations the error in the absence of any classification procedure depends strongly on both the step size and the method used to calculate the new coordinates from the forces. It also depends whether the force is treated as constant between recalculations or whether it is partially recalculated using a rapidly calculated equation. Partial recalculation usually allows the use of a larger $\Delta F_{max}$.

While a small value of $\Delta F_{max}$ could be used that gives negligibly small error in all circumstances, the present invention is preferably implemented by empirically determining a value for $\Delta F_{max}$ that produces an error in the calculation that is approximately the same size as the error from other factors yet small enough that the class calculation procedure does not increase the total error significantly. As mentioned above, the sensitivity factor can be calculated numerically, by changing the coordinates and recalculating the force. The resulting change in the force is called $\Delta F_{numeric}$. If $\Delta F_{numeric}$ is calculated by moving the atoms by approximately the amount they will move on one iteration, then the number of iterations between recalculations can be calculated as:

$$n_{i,j} = \Delta F_{max}/\Delta F_{numeric} \tag{11a}$$

The discussion above has emphasized the use of the sensitivity factor in molecular dynamics calculations. It is equally useful in minimizations. The primary difference between these two applications is the amount the atoms move during an iteration. In molecular dynamics calculations, once the oscillatory nature of the movements is accounted for, the amount of movement per iteration is fairly constant during the course of the calculation. In molecular mechanics minimizations the atoms make relatively large movements at the beginning of the calculation and very small movements at the end.

Because the movements are much smaller at the end of a minimization, the typical interaction can be recalculated much less frequently at the end of the calculation than it can be at the beginning. Since it is common for 90% of the calculation time to be spent getting the last 5% other total energy reduction, the ability provided by the present invention to recalculate the interactions less frequently when the coordinate changes on each iteration are small can make minimizations much faster and cost effective.

Since the sensitivity factor is a derivative of both the energy and the force with respect to the distance, the sensitivity factor could also be simulated using conditional statements and combinations of either the force and distance, combinations of the energy and distance, or combinations of the distance and the parameters that determine an interaction's energy. For example, if for a particular force field the value of the sensitivity factor when $R^{\circ}/R_{i,j} < 1.5$ and $q_i \cdot q_j > 0.25$ indicated that interactions with these properties should be recalculated on every iteration, the following pseudo FORTRAN code could be used to determine the recalculation frequency:

```
IF ((R_0/RIJ.LT.1.5).AND.(Q(I) * Q(J) GT.0.25)) THEN
    RECALCULATION_FREQUENCY (I,J) = 1
ELSE IF (another set of conditions)
    RECALCULATION_FREQUENCY (I,J) = 5
    .
    .
    .
```

The computerized molecular modeling system according to the present invention calculates and utilizes the sensitivity factor, which, as explained above, is a function of the distance and a force field's non-bonded parameters, to perform minimizations and quickly generate an accurate graphical representation of the most likely structure of a molecule, especially large molecules, which have several thousand atoms.

Equations (4) to (7) above summarize how to calculate sensitivity factor for non-bonded interactions in terms of the distance between the atoms. However, in accordance with a further embodiment of the present invention, it could be computationally convenient to use Rsq, the square of the distance, where distance is calculated using the following equations:

$$R_{i,j} = Sqrt \, [Rsq_{i,j}] \quad (12)$$

$$Rsq_{i,j} = (X_i - X_j)^2 + (Y_i - Y_j)^2 + (Z_i - Z_j)^2 \quad (13)$$

X, Y, and Z are the Cartesian coordinates of the atoms. When Rsq is used instead of R, equation (5) becomes:

$$\begin{aligned} S' &= |\partial F_{nb}/\partial Rsq| \\ &= |\partial(\nabla E_{nb})/\partial Rsq| \end{aligned} \quad (14)$$

The equation corresponding to equation (7) is:

$$S' = |\partial F_{nb}/\partial Rsq| + |(\partial^2 F_{nb}/\partial^2 Rsq)| \cdot \Delta Rsq \quad (14a)$$

The equation corresponding to equation (6) is then:

$$s'_{i,j} = Abs[(1.5Q_i q_j)/Rsq^{5/2}_{i,j} + (24A_{i,j}R^{O6}_{i,j})/Rsq^5_{i,j} + (84B_{i,j}R^{O12}_{i,j})/Rsq^8_{i,j}]R_{i,j} \quad (15)$$

The equation corresponding to equation (9) becomes:

$$F_{max} = S'_{i,j} \cdot \Delta Rsq \quad (16)$$

The value of $\Delta Rsq$ can then be approximated by:

$$\Delta Rsq = (Abs[(X^0_i - X^0_j)\Delta X_{i,j} + (Y^0_i - Y^0_j)\Delta Y_{i,j} + (Z^0_i - Z^0_j)\Delta Z_{i,j}]) \cdot n \quad (17)$$

Where X, Y, and Z are the current values of the coordinates and $\Delta X_{i,j}$ is the amount $(X_i - X_j)$ changes between recalculations of the force; $\Delta Y_{i,j}$ and $\Delta Z_{i,j}$ are the changes in $(Y_i - Y_j)$ and $(Z_i - Z_j)$, respectively; and n is the number of steps between recalculations. The oscillatory nature of atomic movements has the same effect on $\Delta X_{i,j}$, $\Delta Y_{i,j}$, and $\Delta Z_{i,j}$ as it does on the $\Delta l_{i,j}$ for equations (10) and (11).

The non-bonded portion of the energy equation in FIG. 3 is a function of distance only and the discussion above implies that this is the case for all non-bonded interactions. However, some force fields have non-bonded interactions that are a function of both distance and orientation. For example, some force fields contain dipole-dipole interactions and some have orientation dependent H-bond interactions.

Because it takes more than two atoms to define an orientation, orientation dependent interactions must include more than two atoms. As a result, there is in principle a different sensitivity factor for each atom making up an orientation-dependent interaction.

The present invention can also be used for force fields that have orientation dependent non-bonded interactions. One way to deal with such force fields is to take advantage of the fact that there are usually fewer orientation dependent interactions than orientation independent interactions. Thus, in accordance with an embodiment of the present invention, the sensitivity factor is used only on the orientation independent interactions while orientation dependent interactions are either recalculated on every iteration or recalculated using a cut-off distance based method.

In accordance with another embodiment of the present invention, the sensitivity factor, equation (5) or (14), is evaluated for the orientation that is most sensitive to changes in atomic positions. One way to determine the orientation with the greatest sensitivity is to take the derivative of the interaction's sensitivity factor with respect to the orientation and then determine the value of the orientation that maximizes the derivative. This value of the orientation is then substituted into the equation for the sensitivity factor. In accordance with another embodiment of the present invention, the sensitivity factor, equation (4a), (5), (7), or (14), is calculated for the current orientation, but a higher recalculation frequency is assigned to each value of the sensitivity factor than would be assigned for an interaction that had no orientation dependence.

In accordance with a still further embodiment of the present invention, an orientation dependent sensitivity factor is calculated by taking the derivative of the force with respect to both distance and orientation. The recalculation frequency is then determined by using, instead of equation (9) or (16), a Taylor's series that contained both distance and orientation terms.

Yet another way to deal with orientation dependent functions is to use equation (4b) and numerically determine the sensitivity factor. One limitation of the numeric method is that the sensitivity factor for orientation dependent interactions is usually anisotropic, which means that the same amount of movement but in different directions can produce different sensitivity factors. Thus the changes in the atomic coordinates used to calculate the numeric sensitivity factor should be in approximately the same direction as the changes that actually occur during the calculation or one should be more conservative in how the sensitivity factor is used when assigning interactions to recalculation classes. The sensitivity factor can also be estimated numerically by keeping track of the forces and how they change over several iterations and then assuming that the changes in the future will be similar to those that occurred in the recent past.

The preceding discussion has concentrated on the sensitivity of the forces to movement of the atoms and how this necessitates the periodic recalculation of forces. However, the sensitivity factor also changes as the atoms move. As a result, each interaction's sensitivity factor and recalculation frequency should be redetermined periodically.

One way to address the sensitivity of the sensitivity factor to changes in the distance between atoms is to calculate its derivative with respect to distance and then use this factor to determine how often the sensitivity factor should be recalculated. While other recalculation frequencies will probably work, it has been found that it is sufficient to recalculate an interaction's sensitivity factor and recalculation frequency after five to twenty-five full evaluations of its force. For example, the recalculation frequency of interactions that are fully recalculated every five iterations is redetermined after 25 to 125 iterations and the recalculation frequency of interactions that are recalculated every 125 iterations is redetermined after 625 to 3125 iterations.

As set forth above, to minimize computational time and costs, the frequency with which a non-bonded interaction is fully recalculated should match the sensitivity of its force to changes in the positions of the atoms. To implement such a match in a minimization program or a molecular dynamics program in the computerized molecular modeling system according to the present invention, the time when each interaction is to be fully recalculated is determined. Since calculating the sensitivity factor takes approximately as long as calculating the forces, substantial amounts of computer time will be saved if the sensitivity factor is calculated only occasionally and the recalculation frequency derived from it saved in the system's memory.

In accordance with the present invention, the recalculation frequency for each interaction can be kept in an array or list that is searched on each iteration for interactions that need to have their forces recalculated. This method is practical for small and medium sized molecules. This method can also be used for large molecules and large aggregates of molecules, but the cost is substantially greater because such an array or list would have to be able to hold at least $n^2/2$ elements, where n is the number atoms. If, for example, there are 10,000 atoms, an array would have to be 200,000,000 bytes long if an array of standard integers, which are 4 bytes long, were used and 400,000,000 bytes if a linked list were used. In addition, searching through such a large array or list could take substantial amounts of computer time.

In accordance with another embodiment of the present invention, each interaction is assigned to one of several classes based on its recalculation frequency. For example, interactions that should be recalculated after 1 to 4 iterations could be assigned to the A-class, interactions with recalculation frequencies of once every 5 to 24 iterations could be assigned to the B-class, interactions with recalculation frequencies of once every 25 to 124 iterations could be assigned to the C-class and interactions that need to be recalculated only once every 125 iterations or less could be assigned to the D-class. Then, the system could fully recalculate all those interactions in the A-class on every iteration, those in the B-class every 5 iterations, those in the C-class every 25 iterations, and those in the D-class every 125 iterations. It should be clear, moreover, that other combinations of recalculation frequencies and/or numbers of classes are also possible.

In accordance with a further embodiment of the present invention, the forces due to interactions that are not fully recalculated on each iteration are not treated as constant between full recalculations but are approximated using an equation. This equation is a function of the number of iterations since the last full recalculation. An algebraic equation is one type of equation that could be used:

$$F_{ap} = C_0 + \sum_{k=1}^{m} C_k n^k \quad (18)$$

Where $F_{ap}$ is an approximation of the force due an interaction, $C_0$ is the force on the last full recalculation, n is the number of iterations since the last full recalculation, and m is the degree of the equation.

The coefficients in equation (18), $C_k$, can be determined, using methods known to those skilled in the art, by fitting the equation to the forces from the previous m+1, or more, full recalculations.

A preferable implementation of the rapidly calculated approximation uses equations that give the sum of the forces acting on an atomic coordinate due to all the interactions in a particular class. Such an implementation is faster than using a separate approximation for each coordinate—interaction combination.

The benefit of this partial recalculation method is that it allows fewer full recalculations to be performed. This reduction can be made use of by assigning interactions to essentially the same classes as when there are no partial recalculations but increasing the number of iterations between full recalculations, or the recalculation frequencies can be kept the same while assigning more interactions to classes with less frequent full recalculations.

The discussion above of the sensitivity factor has emphasized non-bonded interactions because they are the most numerous interactions in the typical molecule. There are, however, numerous other types of interactions to which sensitivity factors can be applied. In the context of this discussion, the major difference between non-bonded and most other interactions is that most other interactions are not functions of distance. Instead, they are functions of some other geometric quantity such as, for example, a torsional angle, which is defined by the relative positions of four atoms. As a result, all of the equations discussed above in which the derivative of the distance or the distance squared were used can not be applied to these interactions. However, $R_{nb}$ and Rsq can be replaced by some other geometric factor in order to obtain the sensitivity factor.

Modifying equation (5) to apply to any interaction, non-bonded or otherwise, the sensitivity factor is:

$$S_{\xi_{-i}} = |\partial(\nabla E)/\partial \xi| \quad (19)$$

Where $S\xi_{-i}$ is the sensitivity factor for $i^{th}$ atom in an interaction, which may or may not be a non-bonded interaction, and $\xi$ stands for some arbitrary interaction that atom i is apart of.

Note that unlike the orientation independent non-bonded case, where the sensitivity factor has the same value for all the atoms making up the interaction, when the geometric factor that defines an interaction is defined by more than two atoms there is generally a different sensitivity factor for each atom.

In principle these different sensitivity factors mean that each atom making up an interaction has a different recalculation frequency. In practice, once the force acting on one of the atoms in an interaction has been calculated, the additional computational effort required to calculate the forces acting on the other atoms is usually so small that it is usually worthwhile to calculate all the forces due to the interaction whenever one of these forces is needed. Thus, for example, the largest of a torsional interaction's sensitivity factors can be used to assign it to a recalculation class and recalculated all its forces, even the ones that vary slowly, whenever the most sensitive force needs to be recalculated.

The numeric calculation of the sensitivity factor, which can be done by replacing $\Delta R_{nb}$ in equation (4a) with $\Delta \xi$, can also be applied to interactions other than non-bonded interactions. Numeric calculation is especially convenient for torsional angles because in this case equation (19) gives four different equations for the sensitivity factor, one for each of the atoms, and each of these equations is complex. Numerical calculation of the sensitivity factor can be used to calculate the four different factors without having to develop, program and debug four complex equations.

An atomic sensitivity factor is the scalar magnitude of a vector. This vector has three components, one for each of the atom's coordinates and the scalar magnitude is calculated from these components by taking the square root of the vector's dot product. Thus it is possible to assign interactions to recalculation classes using the elements of the vector. For example, one could assign a torsional interaction to a recalculation class based on the magnitude of the largest of its 12 sensitivity factor vector elements. (There are 12 vector elements because a torsional interaction has 4 atoms and each atom has 3 coordinates.)

C. The Molecular Dynamics Method According to the Present Invention

A further embodiment of the present invention incorporates sensitivity classes into a MD method according to the present invention. The MD method according to the present invention is a member of the class of methods known as predictor-corrector methods. On each full step of a predictor-corrector method, data obtained on previous MD steps is used to calculate the coordinates for the current step. This is called the predictor step. Then the forces are calculated using the coordinates from the predictor step and then these forces, along with those from previous steps, are used to make a second, more reliable calculation of the coordinates. This second calculation of the coordinates is called the corrector step. With previous MD methods it has been found that it is not cost effective to make more than one corrector step for each full step.

In the MD method according to the present invention integrals of cubic force equations, one for each atomic coordinate, are used to calculate the coordinates and velocities of the atoms:

$$F_i = a_i + b_i \cdot t + c_i \cdot t^2 + d_i \cdot t^3 \qquad (20)$$

where i stands for an atomic coordinate and t stands for the time in units of a single MD step.

These force equations can be calculated from the forces from four MD points using standard methods for solving simultaneous linear equations.

The MD method according to the present invention differs from previous predictor-corrector methods in several ways:

Each full step has many corrector steps.
   It uses sensitivity classes.
   On each corrector step the forces of only selected classes are recalculated.
   In calculating the force equation for the current point, the forces from the next step as well as the forces from the current and previous point are used.

The forces acting on each atom are divided into three classes based on their sensitivity:

Bonds, which are the most sensitive interactions.

A class called Constant, which are interactions whose forces do not change significantly as a result of coordinate changes of the size that occur in going from the coordinates produced by the predictor step to the final, refined coordinates. This class includes most, but not all, non-bonded interactions and most, but not all, torsional interactions. Note that all of the classes discussed above which are not fully recalculated on each step are subsets of the Constant class, but that the Constant class also includes some interactions that should be recalculated on each iteration.

A class called Sensitive, which are interactions, like bond angles, that are much less sensitive than Bonds but more sensitive than Constant interactions. While these interactions may be calculated more than once during a step, they are calculated much less frequently than Bonds. Note that the class of interactions discussed in previous embodiments of the present invention that are recalculated fully on each step are subdivided between the Constant and Sensitive Classes.

It is also useful to create a class called Other, which is the union of the Sensitive and Constant classes, and thus contains all interactions other than Bonds.

Each full step of the MD method according to the present invention includes two substeps, called the extension and refinement substeps, respectively. During the extension substep an estimate of the next step's forces and coordinates is obtained. The time associated with the next step is 2 MD step units beyond the point assigned time t=0. Thus it is called the t=+2 point. On the extension and refinement substeps the force equations are calculated using the forces from the t=−1, t=0, t+1 and t+2 points.

Figure 4:
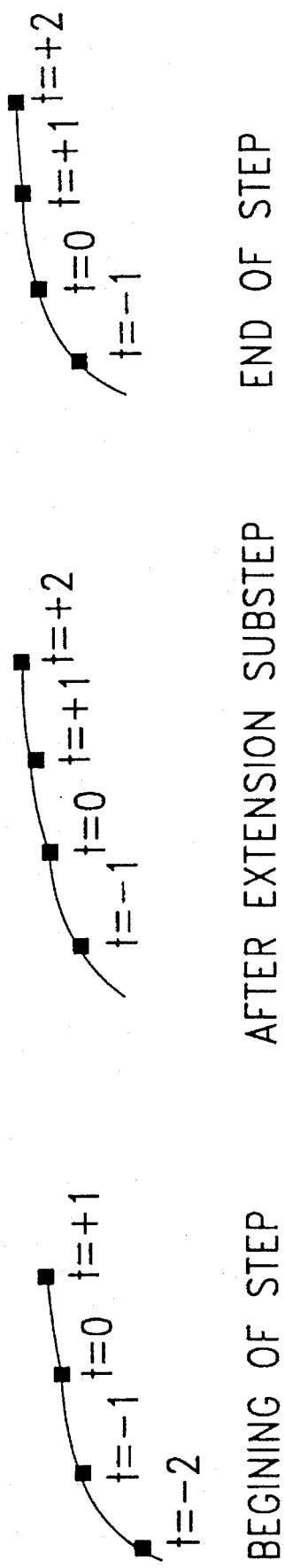
FIG. 4 identifies the points that are considered reliable at various times during a full step of a MD method according to the present invention.

FIG. 4 illustrates the change in the status of the points during a full step of the MD method according to the present invention. Referring to FIG. 4, the line represents the MD trajectory and the points on the line represent the points calculated by the MD algorithm. At the start of the step the MD point from which the step begins is assigned the time t=0. This was the previous step's t=+1 point. The bold line identifies the part of the trajectory for which reliable trajectory points have been calculated. The light line identifies the points for which there is calculated information, but the information is not completely reliable. Note that the previous step's t=+2 point is the current step's t=+1 point and that at the end of the step, the t=+1 point has been converted from a partially refined point to a fully refined one.

Both the extension and refinement substeps include several corrector steps. Each corrector step comprises the following 4 substeps: (1) The most recently calculated set of force equations is used to calculate a new set of coordinates. Because the t=+1 coordinates are not considered reliable, all calculations of coordinates use an integral that starts from the either the t=−1 or t=0 points. (2) The new coordinates are used to calculate the forces associated with one or more classes of forces. (3) The total force for each atomic coordinate is calculated by adding the forces from all three classes. For the classes that were not calculated on this corrector step, previously calculated forces are used. (4) Finally a new set of force equations is calculated.

Each full step is initialized as follows:

A set of force equations for the Other forces is calculated using the Other forces from the t=−2, t=−1, t=0 and t=+1 points.

The Other forces for the t=+2 point are estimated using the Other force equations.

A predictor step is performed which calculates the t=+2 coordinates. For this calculation it is expeditious to integrate force equations obtained by replacing the constant, or $a_i$, term in force equations calculated on the previous step with the current t=0 force.

Calculating the Bond forces and adding them to the estimated Other forces to obtain a set of t=+2 total forces. These t=+2 forces are used along with the t=−1, t=0, and t=+1 forces to calculate a set of force equations.

Each extension substep is performed as follows:

Doing zero or more corrector steps of the t=+2 coordinates in which only the Bond forces are calculated.

Doing a corrector step of the t=+2 coordinates in which all the forces are calculated.

Doing one or more corrector steps of the t=+2 coordinates in which only the Bond forces are calculated.

Next the refinement substep is done. This step is performed as follows:

Doing a corrector step of the t=+1 coordinates in which only the Bond forces are calculated.

Calculating the difference between current and previous Bond forces for each coordinate. Refinement is completed if the largest difference is less than about 0.1 kcal/(angstrom *mole).

If refinement is not complete, doing a corrector step of the t=+1 coordinates in which the Bond and Sensitive forces are calculated.

Returning to the start of the refinement step.

After the refinement of the t=+1 coordinates and forces is complete, the t=+1 velocity is calculated.

Note that while both the MD method according to the present invention and previously described embodiments of the invention use sensitivity classes, they use them in different ways. The previous embodiments use classes to determine which interactions do not change significantly when going from one step to another and thus do not have to be fully recalculated on each step. The MD method according to the present invention uses sensitivity classes to decide how often each interaction will be recalculated during a single MD step. Of course, any interactions whose sensitivity is low enough that its force does not change significantly as a result of the coordinate changes that occur between steps will not change significantly as a result of the changes that occur during refinement of the coordinates during a step. However, many interactions that do change significantly between steps can nevertheless be assigned to the MD method's Constant class because they do not change significantly as a result of the changes that occur during refinement of a single step.

The MD method according to the present invention and the previously described embodiments can be profitably implemented independently of each other. For example, the previous embodiments of the present invention can be used with standard MD methods, and, in addition, the MD method according to the present invention can be used with prior art methods for calculating the forces. In each case, the result is an implementation that is faster than the prior art methods alone. Of course, the maximum benefit is obtained if both embodiments are used together.

A preferred embodiment of the invention implements both the non-bond recalculation classes and the MD method according to the present invention and uses classes of non-bonded interactions:

Non-bond class 1 is a subset of the Sensitive class.

Non-bond class 2 is a subset of the Constant class and is fully recalculated on every step.

Non-bond class 3 is a subset of the Constant class and is fully recalculated every other step. Between full recalculations it is approximated by a quadratic equation.

Non-bond class 4 is a subset of the Constant class and is fully recalculated every 4 steps. Between full recalculations it is approximated by a linear equation.

Non-bond class 5 is a subset of the Constant class and is fully recalculated every 25 steps. It is treated as constant between full recalculations.

The criteria used to assign interactions to each class were determined by starting with stringent criteria and then systematically using less and less stringent criteria until a noticeable decrease in the accuracy of the calculation as determined by the change in the total energy over several steps was seen. Then the criteria were returned to the last set of criteria that had no noticeable effect on the accuracy. These tests were performed using the Sybyl force field with a 177 atom peptide using a test case kindly supplied by P. A. Cruickshank. This test case ignored all non-bonded interactions between atoms separated by more than 12 angstroms.

The following pseudo FORTRAN code summarizes the assignment criteria:

If ((DelFor5 .LT. 0.01) .AND. (R12 .GT. 4.5)) Then
  This is a Class 5 interaction
Else If ((DelFor4 .LT. 0.01) .AND. (R12 .GT. 4.0)) Then
  This is a Class 4 interaction
Else If ((DelFor3 .LT. 0.01) .AND. (R12 .GT. 3.5)) Then
  This is a Class 3 interaction
Else If ((DelFor2 .LT. 0.2) .AND. (R12 .GT. 2.5)) Then
  This is a Class 2 interaction
Else
  This is a Class 1 interaction
End If In this code R12 is the distance between the two atoms making up the non-bonded interaction, the DelFor terms are the estimated change in the force to the next full recalculation of the class given by the trailing number. The DelFor3, DelFor4, and DelFor5 terms were calculated using Equation (14a) in equation (9), while DelFor2 was calculated using Equation (14) in Equation (10). The value of ΔRsq used in equation (10) was calculated using equation (17) where n is the number of steps between full recalculations and where the ΔX, ΔY, ΔZ were calculated using the larger of the instantaneous difference velocity of the two atoms and the velocity calculated using the mass adjusted average speed.

The interactions for classes 1 to 4 are held in lists while the interactions for class 5 are held in a packed bit set. Classes 1 to 4 are reclassified as a group every 50 iterations and class 5 is reclassified every 250 iterations. Note that all interactions are reclassified when class 5 is reclassified.

The Sybyl force field treats 1-4 non-bonded interactions slightly differently than it does other non-bonded interactions. Only Class 1 and Class 2 were used for 1-4 interactions but otherwise the criteria used to assign them to classes was the same as for other types of non-bonded interactions. Thus the pseudo code for 1-4 class assignment is:

If ((DelFor2 .LT. 0.2) .AND. (R12 .GT. 2.5)) Then
  This is a Class 2 1-4 interaction
Else
  This is a Class 1 1-4 interaction
End If The 1-4 non-bonded interactions are reclassified every 25 steps.

This preferred embodiment also uses two classes of torsional interactions.

Class A is a subset of the Sensitive class.

Class B is a subset of the Constant class and as such was recalculated at least once fore each MD point.

Torsional interactions are assigned to these classes by calculating the three components of $\Delta F_i$ for each of the four atoms making up the torsional angle and determining which component has the largest absolute value. If this largest component is larger than 0.05 kcal/angstrom the interaction was assigned to Class A, otherwise it is assigned to Class B. The components are determined by calculating the initial force along each coordinates of the 4 atoms making up the torsion, moving all the coordinates by one tenth of the estimated change in going from one step to the next and then recalculating the forces. These estimated coordinate changes are calculated by multiplying the mass weighted average speed by one tenth of the step size.

D. The Data Compression System According to the Present Invention

In accordance with a further embodiment of the present invention, information regarding the interactions that are in each class is kept in arrays or lists that are divided by class. This eliminates the need to spend computer time searching a large array on each iteration since the array for a particular class would be accessed only when all the interactions in it were to be recalculated. The drawback of this embodiment is that the total memory required to store the information is at least as large as if the recalculation frequencies were kept in a single array.

This drawback is greatly reduced in accordance with a further embodiment of the present invention. In accordance with this embodiment, bit sets are used to hold the information regarding which interactions belong to each class. For example, if the 117th bit in the B-class set is "1" the 117th interaction is a member of the B-class. If the bit is set to "0", then the 117th interaction is not a member of the B-class.

The use of bit sets, in which only a single bit is used for each interaction, is known in the art and allows the amount of computer memory used to hold a single number to hold information on as many interactions as the number of bits in it. The amount of memory used to hold a number is called a computer word. The number of bits in a computer word varies but is often 32. Thus a bit set for a molecule with 10,000 atoms would require the amount of computer memory occupied by about 1,652,500 numbers to identify which members were members of a particular class. However, since one bit set is needed for each class, a 10,000 molecule would require memory for 6,250,000 numbers to hold bits sets if four classes were used While memory for 6,250,000 numbers is a significant reduction from the memory for 200,000,000 numbers needed if bit set were not used, it is still a substantial amount of memory.

The amount of memory required for a bit set can be further reduced in accordance with another embodiment of the present invention if the bit set is compressed. While a number of prior art data compression techniques could be useful in this regard, such as those discussed in Storer, J. A. "Data Compression: Methods and Theory", Computer Science Press (1988), in accordance with a data compression technique according to the present invention, the features present in most molecular mechanics calculations are used to provide a particularly effective reduction in the amount of memory required to hold a class' bit set.

In accordance with standard practice, atoms in a molecular mechanics calculation are assigned a number and the numbering procedure used in most large molecules results in atoms separated by only a few bonds being assigned similar numbers. Since atoms separated by only a few bonds must be in approximately the same region of space, their interactions with some other atom will tend to be assigned to the same one or two recalculation classes.

The purpose of using recalculation classes is to reduce the recalculation frequency as much as possible. Thus all recalculation classes, except for the least frequently calculated class, should have relatively few members. Thus, most of the bits in the sets used in conjunction with the present invention will be 0 bits. The fact that atoms with similar atomic numbers will tend to be assigned to the same one or two classes means that a set's comparatively few 1 bits will be clustered in only a few words of computer memory. In accordance with the data compression method of the present invention, words containing only 0 bits are eliminated and only the words containing 1 bits are retained.

In cases where the forces acting on all the atoms are calculated before any of the atoms are moved, further memory space can be saved by using the standard practice of recording each interaction once, namely as an interaction between a lower numbered atom and a higher numbered atom. Thus, for example, the interaction between atoms 2 and 5 can be recorded as an interaction between atom 2 and atom 5. The fact that atom 5 has an interaction with atom 2 need not be recorded separately. Note that since the 1-2 and 2-2 interactions are not recorded as one of atom 2's interactions, the 2-3 interaction is atom 2's first interaction and the 2-5 interaction is its third interaction.

In accordance with the data compression method according to the present invention, a compressed bit set for a particular class can be generated by creating a bit set for each atom that identifies which of the atom's interactions belong to the class. Then these individual bit sets are concatenated into a single bit set to create the full, concatenated set for the class. After the bits sets have been concatenated, the words that contain non-zero bits are identified and saved in an access list. The words containing only zero bits are discarded and the remaining words saved in another array. Together the access list and the array containing the non zero words comprise the concatenated, compressed bit set. Then, during processing of the bit set, the computerized molecular modeling system knows that any word not identified in the access list contains only zero bits and acts accordingly. Words containing non zero bits, which are kept in the compressed set, are processed in the same way as if the full bit set were being used.

The concatenated, compressed bits set can also be generated by processing the atoms sequentially. In this method as each atom is processed its full bit set is generated, compressed and added to the concatenated, compressed bit set. Thus each atom's bit set is compressed and added to the concatenated, compressed bit set before processing of the next atom begins. The advantage of this method over the previous method of generating the concatenated, compressed set is that since the full, concatenated bit set never exists, memory does not need to allocated for it.

This compression method can be implemented using two arrays, which we will call ACCESS_LIST and BITS:

ACCESS_LIST identifies the elements in the full concatenated bit set that contain non zero elements. It is designed to be processed starting with atom 1, then atom 2, . . . atom N.

BITS contains the non zero elements of the full, concatenated bit set.

If, for example, the value of ACCESS_LIST (4) is 12, it means that the 12th word in the full, concatenated set is the 4th non-zero word in the set and that BITS (4) contains this 12th word. As such, assuming 4 bits per word, and a molecule with 10 atoms; atom 1 would have 9 potential interactions (1-2, 1-3, . . . 1-10) and its full bit set would require 3 words (interactions 1-2 to 1-5 go in the first word, 1-6 to 1-9 in the second word, and 1-10 is the only interaction in the third word). Atom 2 has 8 potential interactions, atoms 3 has 7, and so on. Thus the bits sets for atoms 2 to 5 would each require 2 words, and the bit sets for atoms 6 to 9 would require 1 word each. Thus the full, concatenated bit set would require 1*3+4*2+4*1=15 words. The 4th word in the full, concatenated bit set would be the 1st word in atom 2's bit set and would be for its interactions with atoms 3 to 6.

This data compression method will now be demonstrated for a molecule with 315 atoms. This example assumes that the computer used allows 31 bits in each word to be used for bit sets. Thus the full bit set for each of this molecule's first 4 atoms will be 11 words long.

Figure 6:
FIG. 6 is a graphical representation of part of an array containing a full concatenated bit set before it is compressed in accordance with the present invention.
Figure 6:

A graphical representation of a portion of the array containing the full concatenated bit set is shown in FIG. 6.

The ACCESS_LIST and BITS arrays comprising the compressed version of this bit set would be:

ACCESS_LIST (1) = 1
ACCESS_LIST (2) = 4
ACCESS_LIST (3) = 10
ACCESS_LIST (4) = 12
ACCESS_LIST (5) = 16
ACCESS_LIST (6) = 20

.
.

ACCESS_LIST (n − 1) = the number of the last non-zero word in the full concatenated bit set.
ACCESS_LIST (n) = a number larger than the number of words in the full concatenated bit set that is used to indicate the end of meaningful data in the array.
BITS (1) = The first word of the full concatenated bit set, which is the first word of atom 1's full bit set.
BITS (2) = The fourth word of the full concatenated bit set, which is the fourth word of atom 1's full bit set which corresponds the interactions of atom 1 with atoms 95 to 125 since each of the 31 bits of the fourth word corresponds to a different interaction.
BITS (3) = The tenth word of the full concatenated bit set, which is the tenth word of atom 1's full bit set.
BITS (4) = The twelfth word of the full concatenated bit set, which is the first word of atom 2's full bit set.
BITS (5) = The sixteenth word of the full concatenated bit set, which is the fifth word of atom 2's full bit set.
BITS (6) = The twentieth word of the full concatenated bit set, which is the ninth word of atom 2's full bit set.
BITS (n − 1) = last non-zero word in the full concatenated bit set.

This compression method assumes that most of the bits are zero. However, the bit set for at least one class, preferably the least frequently calculated one, will contain mainly 1 bits. This need not be a problem because such a bit set can be convened to a set containing mainly zeros by reversing the meaning of a 0 and 1 bit. For example, if most interactions are members of the least frequently calculated class, a 1 bit in this class set could be defined to indicate an interaction that is NOT a member of the class. This will convert the bit set from one containing mainly 1 bits to one containing mainly 0 bits and the resulting set can be compressed using this method.

What is claimed is:

1. A method for generating an image of a likely structure of a molecule, comprising the steps of:

(a) accepting as input into a computer an initial structure of the molecule, the initial structure of the molecule including a set of atom coordinates for the molecule;

(b) generating a set of interactions for each atom, each interaction corresponding to a force between its respective atom and one or more other atoms in the molecule;

(c) determining, from the initial structure of the molecule, a set of qualifying interactions and a set of non-qualifying interactions, the total set of interactions being a super-set of the set of qualifying interactions and the set of non-qualifying interactions;

(d) calculating a sensitivity factor for each interaction of the set of qualifying interactions based upon a sensitivity of the initial force of each interaction of the set of qualifying interactions with respect to changes in the position of the atoms which correspond to said each interaction, each sensitivity factor indicating a recalculation frequency for a respective interaction of the set of qualifying interactions;

(f) performing one of an energy minimization procedure and a molecular dynamics procedure, the step of performing including:

1) calculating a new force for each interaction of the set of interactions for an $n-1^{th}$ structure of the molecule, the step of calculating further including the steps of:
   (a) fully calculating a new force for each interaction of the set of non-qualifying interactions;
   (b) fully calculating a new force for an interaction of the set qualifying interactions if the respective recalculation frequency for said interaction indicates that a previously calculated force is invalid;
   (c) using a previously calculated force as the new force for an interaction of the set of qualifying interactions if the recalculation frequency for said interaction indicates that the previously calculated force is valid;
  2) calculating a new total force for each atom by summing the new forces from all the interactions corresponding to said each atom;
  3) using the new total forces for the $n-1^{th}$ structure of the molecule to calculate an $n^{th}$ structure of the molecule;
  4) repeating step (f)(1–2) for n=1 through X interactions to generate X possible structures of the molecule, (g) generating the image of the likely structure of the molecule, or a representative structure, or a sequence of structures based upon one or more of the X possible structures of the molecule.

2. A method for generating an image of a likely structure of a molecule, comprising the steps of:

(a) accepting as input into a computer an initial structure of the molecule, the initial structure of the molecule including a set of atom coordinates for the molecule;

(b) generating a set of interactions for each atom, each interaction corresponding to a force between its respective atom and one or more other atoms in the molecule;

(c) determining, from the initial structure of the molecule, a set of qualifying interactions and a set of non-qualifying interactions, the total set of interactions being a super-set of the set of qualifying interactions and the set of non-qualifying interactions;

(d) calculating a sensitivity factor for each interaction of the set of qualifying interactions based upon a sensitivity of the initial force of each interaction of the set of qualifying interactions with respect to changes in the position of the atoms which correspond to said each interaction, each sensitivity factor indicating a recalculation frequency for a respective interaction of the set of qualifying interactions;

(f) performing one of an energy minimization procedure and a molecular dynamics procedure, the step of performing including:

1) calculating a new force for each interaction of the set of interactions for an $n-1^{th}$ structure of the molecule, the step of calculating further including the steps of:
   (a) fully calculating a new force for each interaction of the set of non-qualifying interactions;
   (b) fully calculating a new force for an interaction of the set qualifying interactions if the respective recalculation frequency for said interaction indicates that a previously calculated force is invalid;
   (c) using an approximation for the new force for an interaction of the set of qualifying interactions if the recalculation frequency for said interaction indicates that the approximation invalid, said approximation being one of a previously calculated force, and a force calculated using a rapidly calculated equation;

2) calculating a new total force for each atom by summing the new forces from all the interactions corresponding to said each atom;
3) using the new total forces for the n−1$^{th}$ structure of the molecule to calculate an n$^{th}$ structure of the molecule;
4) repeating step (f)(1–2) for n=1 through X interactions to generate X possible structures of the molecule, (g) generating the image of the likely structure of the molecule, or a representative structure, or a sequence of structures based upon one or more of the X possible structures of the molecule.

3. The method according to claim 2 wherein the sensitivity factor is defined as $$S_{\xi-i} = |\partial F_i / \partial \xi_i|$$

where $F_i$ is the force due to an interaction that acts on atom i, and $\xi_i$ is a geometric factor that partially or completely determines the force of the interaction.

4. The method according to claim 2 wherein each qualifying interaction is a non-bonded interaction for which the sensitivity factor is defined as $$S = |\partial F_{nb} / \partial R_{nb}|$$

where $F_{nb}$ is the force due to the interaction, and $R_{nb}$ is the distance between the two atoms making up the interaction.

5. The method according to claim 2 wherein the sensitivity factor is defined as $$S_{\xi-i} = |\Delta F_i / \Delta \xi_i|$$

where $F_i$ is the force due to the interaction that acts on atom i, and $\xi_i$ is a geometric factor that partially or completely determines the force acting on atom i due to the interaction.

6. The method according to claim 2 where in the sensitivity factor is defined as $$S^p{}_{\xi-i} = |\Delta F_{\xi-i}|$$

where $|\Delta F_{\xi-i}|$ is the change in the force due to an interaction that acts on atom i that occurs when a geometric factor, $\xi-i$, that partially or completely determines the force acting on atom i due to the interaction is changed.

7. The method according to claim 2 wherein the qualified interaction is a non-bonded interaction for which the sensitivity factor is defined as $$S = |\Delta F_{nb} / \Delta R_{nb}|$$

where $\Delta F_{nb}$ is a change in the force for an interaction that is a function of the distance between the atoms making up the interaction, and $\Delta R_{nb}$ is the change distance between the atoms.

8. The method according to claim 2 wherein the qualified interaction is a non-bonded interaction for which the sensitivity factor is defined as $$S^P = |\Delta F_R|$$

where $\Delta F_R$ is a change in the force for an interaction that is a function of the distance between the atoms making up the interaction, and $\Delta R$ is the change distance between the atoms.

* * * * *